(12) United States Patent
McKenna et al.

(10) Patent No.: US 6,444,837 B1
(45) Date of Patent: Sep. 3, 2002

(54) SYNTHESIS AND ANTIVIRAL ACTIVITY OF A SERIES OF PYROPHOSPHATE ANALOGS

(75) Inventors: Charles E. McKenna, Pacific Palisades, CA (US); Zeng-Min Li, New York, NY (US); Xue-Wei Liu, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/535,252

(22) Filed: Mar. 23, 2000

Related U.S. Application Data

(63) Continuation-in-part of application No. 09/352,237, filed on Jul. 13, 1999.
(60) Provisional application No. 60/092,650, filed on Jul. 13, 1998, and provisional application No. 60/125,805, filed on Mar. 23, 1999.

(51) Int. Cl.⁷ .................................................. C07F 9/00
(52) U.S. Cl. .......................... 558/181; 560/129; 562/24
(58) Field of Search .................. 560/129, 190, 560/195; 558/179, 181; 562/8, 9, 24

(56) References Cited

U.S. PATENT DOCUMENTS

| 3,943,201 A | * | 3/1976 | McIntosh |  |
|---|---|---|---|---|
| 4,033,749 A | * | 7/1977 | McIntosh |  |
| 5,072,032 A | * | 12/1991 | McKenna | 562/9 |
| 6,002,029 A | * | 12/1999 | Hostetler et al. | 554/49 |

OTHER PUBLICATIONS

Helbig et al Antiviral Research 10 pp. 99–106.*
CA:92:175780 abs of US986003 defensive publication by Barrier Sep. 1979.*
CA:72:5004 abs of Tr. Khim–Met Inst Akad Nauk Kaz SSR by Radenkova et al 5 pp 47–9 1969.*
CA:123:9544 abs of Zh. Obshch Khim by Kovalenko et al 64(10) pp 1634–8 1994.*
CA:124:56067 abs of Tetrahedron Lett 36(37) pp 6759–60 by Salomon et al 1995.*
CA:125:168164 abs of Phosphorus, Sulfur Silicon Relat Elem by Makomo et al 112(1–4) pp 193–202 1996.*
CA:74:112211 abs of DE2040367 Feb. 1971.*
CA:127:103946 abs of J Med Chem by Rosowsky et al 40(16) pp 2482–2490 1997.*
CA:93:182031 abs of J Nucl Med by Wand 21(8) pp 767–70 1980.*
CA:105:17828 abs of IRCS Med Sci by Hutchinson et al 14(2) p 176–7 1986.*
CA:129:53610 abs of EP845217 Jun. 1998.*
CA:932890 abs of Biochim Biophys Acta 607(1) pp 53–64 1980.*

* cited by examiner

Primary Examiner—Jean F. Vollano
(74) Attorney, Agent, or Firm—Fulbright & Jaworski L.L.P.

(57) ABSTRACT

Preparations of pyrophosphate analogues, including phosphonoformic acid, bisphosphonic acid, and phosphonoacetic acid derivatives, exhibiting antiviral activity. Such compounds, are used directly, or as prodrugs, in compositions and methods for treating viral infections, including but not limited to HIV, herpesviruses including HSV, EBV, VZV, CMV, HHV-6 and HHV-8 (Kaposi's sarcoma); HPV; rhinoviruses; and hepatitis-linked viruses. Compounds of the present invention for use as antiviral agents or their intermediates include sulfur-containing, polyhydroxy, and lipophilic derivatives of phosphonoformic acid.

6 Claims, No Drawings

SYNTHESIS AND ANTIVIRAL ACTIVITY OF A SERIES OF PYROPHOSPHATE ANALOGS

CROSS-REFERENCE WITH RELATED APPLICATIONS

This application in a continuation-in-part of U.S. patent application Ser. No. 09/352,237, filed Jul. 13, 1999, which claims the benefit of U.S. Provisional Application No. 60/092,650, filed Jul. 13, 1998. In addition, this application claims the benefit of U.S. Provisional Application No. 60/125,805, filed Mar. 23, 1999.

BACKGROUND OF THE INVENTION

Trisodium phosphonoformate (PFA trisodium salt, Foscarnet), a pyrophosphate analogue, inhibits HIV reverse transcriptase (HIV, RT) with an $IC_{50}$ near 1 $\mu$M, and also inhibits several herpesvirus DNA polymerases including the DNA polymerase of Cytomegalovirus (CMV). In clinical trials of PFA for treatment of CMV infection in AIDS patients, the drug was efficacious but exhibited reversible nephrotoxicity. In one study, a slowed progress to death was also observed, attributed to the anti-HIV effect of the drug. A number of recent studies have suggested Foscarnet deserves consideration for use in anti-HIV combination therapy owing to its HIV resistance pattern, which differs from many clinical anti-HIV agents such as AZT. Foscarnet is broadly active against other viruses as well, including influenza and hepatitis viruses.

Foscarnet has serious disadvantages as a systemic drug. It is known to affect plasma electrolyte concentrations, intestinal phosphate transport, and bone metabolism. Furthermore, Foscarnet must be administered intravenously, owing to its low oral bioavailability. Thus antiviral pyrophosphate analogues with improved pharmacological properties are of great interest.

BRIEF SUMMARY OF THE INVENTION

The present invention solves the above-described problems by providing methods for readily synthesizing a series of pyrophosphate analogues, including sulfur-containing, polyhydroxy, and lipophilic derivatives of phosphonoformic acid. The present invention also provides compositions and methods for treating viral infections, which utilize a series of pyrophosphate analogues, including phosphonoformic, bisphosphonic, and phoshphonoacetate acid derivatives.

These and other features, aspects, and advantages of the present invention will become better understood with regard to the following detailed description and appended claims.

DETAILED DESCRIPTION OF THE INVENTION

The present invention involves the structure, synthesis, and use of a series of potent pyrophosphate analogues, which can serve as effective antiviral compounds or their intermediates. More particularly, we have identified several pyrophosphate analogues which show very high antiviral activity against human herpesvirus 8 (HHV-8).
Phosphonoformic Acid Derivatives
  Thio-Analogues of PFA
  Thio derivatives of organophosphorus compounds have long been of interest to chemists, not least because these compounds can be useful in agriculture or medicine, as well as in synthesis (Edmundson, R. S., *The Chemistry of Organophosphorus Compounds;* John Wiley: New York, 1996). The replacement in a phosphate, phosphonate or phosphinate molecule of one or more oxygen atoms by sulfur may lead to significant alteration in biological activity or related properties. As a class, the sulfur containing phosphonoformate derivatives have received relatively little attention in the literature, although particular examples (chiefly triester) have been made and shown to possess a range of useful applications in synthetic chemistry [Grisley, D. W., *J. Org. Chem.* 26, 2544 (1961); Masson, S. et al., *J. Org. Chem.* 59, 4507 (1992); Masson, S. et al., *Tetrahedron* 50, 10277 (1994); Kovalenko, L. V., et al. *Russ. J. Gen. Chem.* 64,1456 (1994)].

The present invention teaches the synthesis of sulfur-containing phosphonoformic acid derivatives, which are obtained by replacing one or more of the five oxygen atoms of the original phosphonoformate molecule by a sulfur atom.

The analogues have the general formula:

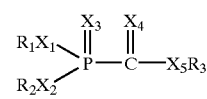

I wherein $R_1$ $R_2$, and $R_3$ are each independently selected from $C_1$–$C_{20}$ alkyl, aryl, H, or cation, $X_1$ $X_2$, $X_3$, $X_4$, and $X_5$ are O or S, provided that:

(a) at least one of $X_1$–$X_5$ is S;
  (b) when $X_1$ is S, then either (i) $R_1$ or $R_2$ is $C_1$–$C_{20}$ alkyl, aryl, or H, or (ii) at least one of $X_2$, $X_3$, $X_4$, and $X_5$ is also S.

The term "$C_1$ to $C_{20}$ alkyl" as used herein and in the claims (unless the context indicates otherwise) means a saturated or unsaturated, branched or straight chain hydrocarbon group having 1 to 20 carbon atoms such as methyl, ethyl, propyl, isopropyl, butyl, isobutyl, t-butyl, etc. Unless otherwise specified in the particular instance, the term "aryl" includes "substituted or unsubstituted phenyl." As used herein and in the claims, "substituted or unsubstituted phenyl" is intended to mean a phenyl group wherein an atom, element or group is regarded as having replaced a hydrogen atom.

The parent structures may also form part of a derived entity wherein $R_1$, $R_2$ and/or $R_3$ are more complex groups than simple alkyl or aryl (or portions of the same molecule), with the parent incorporated via one or more esteratic or ether bonds as indicated above.

As used herein, the "cation" can be a pharmaceutically acceptable alkali metal (e.g., Li, Na, or K), ammonium cation, alkaline earth cation (e.g., $Ca^{2+}$, $Ba^{2+}$, $Mg^{2+}$), higher valency cation, or polycationic counter ion (e.g., a polyammonium cation). See, Berge, et al., "Pharmaceutical Salts", *J Pharm. Sci.* (1977) 66:1–19. It will be appreciated that the stoichiometry of an anionic compound to a salt-forming counterion (if any) will vary depending on the charge of the anionic portion of the compound (if any) will vary depending on the charge of the anionic portion of the compound (if any) and the charge of the counterion. Preferred pharmaceutically acceptable salts include a sodium, potassium or calcium salt, but other salts are also contemplated within their pharmaceutically acceptable range.

Furthermore $R_1$, $R_2$, and $R_3$ may be so designed as to create novel biologically active compounds or prodrugs, wherein one conjugating moiety may be for example a nucleoside or nucleotide with independent activity, and another moiety may be for example a diol, triol or higher polyhydroxy group conferring enhanced cell transport or other desirable properties. The term "prodrug" as used herein and in the claims (unless the context indicates otherwise) denotes a derivative of an active drug which is converted after administration back to the active drug. More particularly, it refers to derivatives of the pyrophosphate analogues of the present invention, which are capable of undergoing hydrolysis or oxidative cleavage of the ester moiety so as to release active, free drug. The physiologically hydrolyzable groups serve as prodrugs by being hydrolyzed in the body to yield the parent drug.

Note, where $R_1=R_2$, $X_1$ and $X_2$ are generally equivalent substitutions. However, compounds wherein $R_1=R_2$, such that $X_1$ and $X_2$ substitutions result in distinct isomers, are also within the scope of the invention. Furthermore, stereoisomers, including stereoisomers created by the possibility of chirality at the phosphorus atom e.g. in a structural fragment like $M^+[R_1O(S)P(O)R_3]^-$ where $M^+$ is a cation are also within the scope of the invention.

We further predict an overall trend of decreasing stability as S replaces O, particularly when $S \geq 3$. Accordingly, for preferred versions of the sulfur-containing PFA derivatives of the present invention, at least two of $X_1$, $X_2$, $X_3$, $X_4$, and $X_5$ will be oxygen.

The most preferred sulfur containing PFA derivatives of the present invention are those which act as antiviral compounds or their intermediates. As a result of initial screening for antiviral activity against HHV-8, we have identified several candidates having a moderate to high therapeutic index for use as effective antiviral compounds. Accordingly the most preferred sulfur containing PFA derivatives of the present invention include compounds having the following structures:

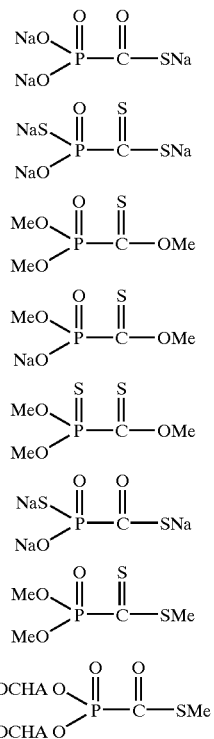

General synthetic pathways as applied to examples of various thio-analogs of PFA are outlined in the following conceptual schemes:

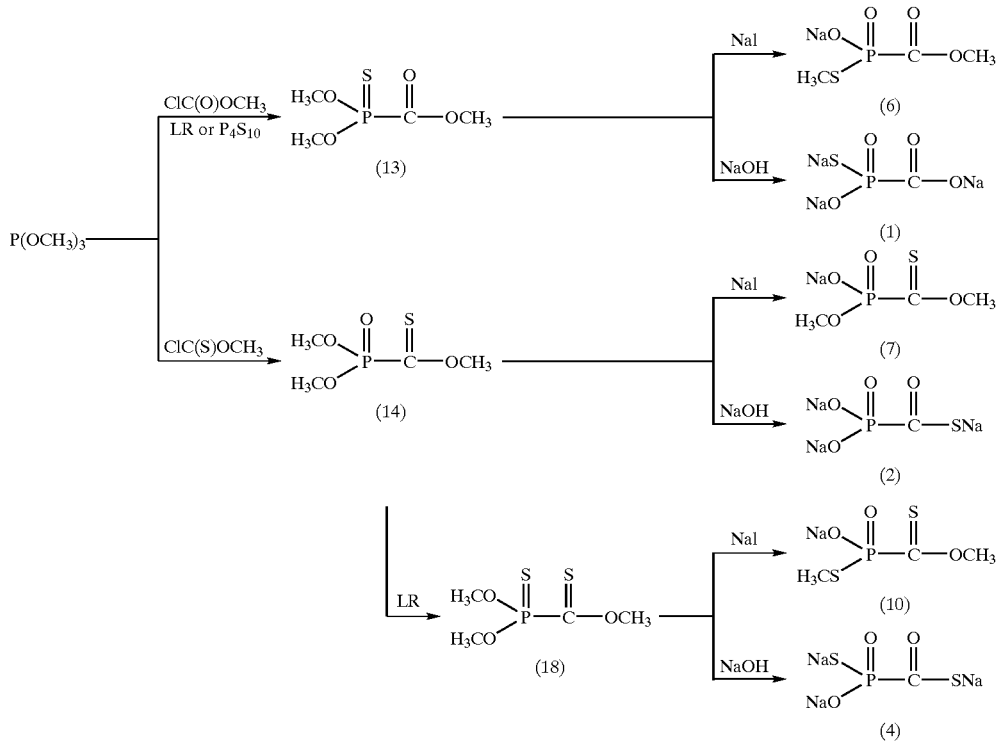

-continued

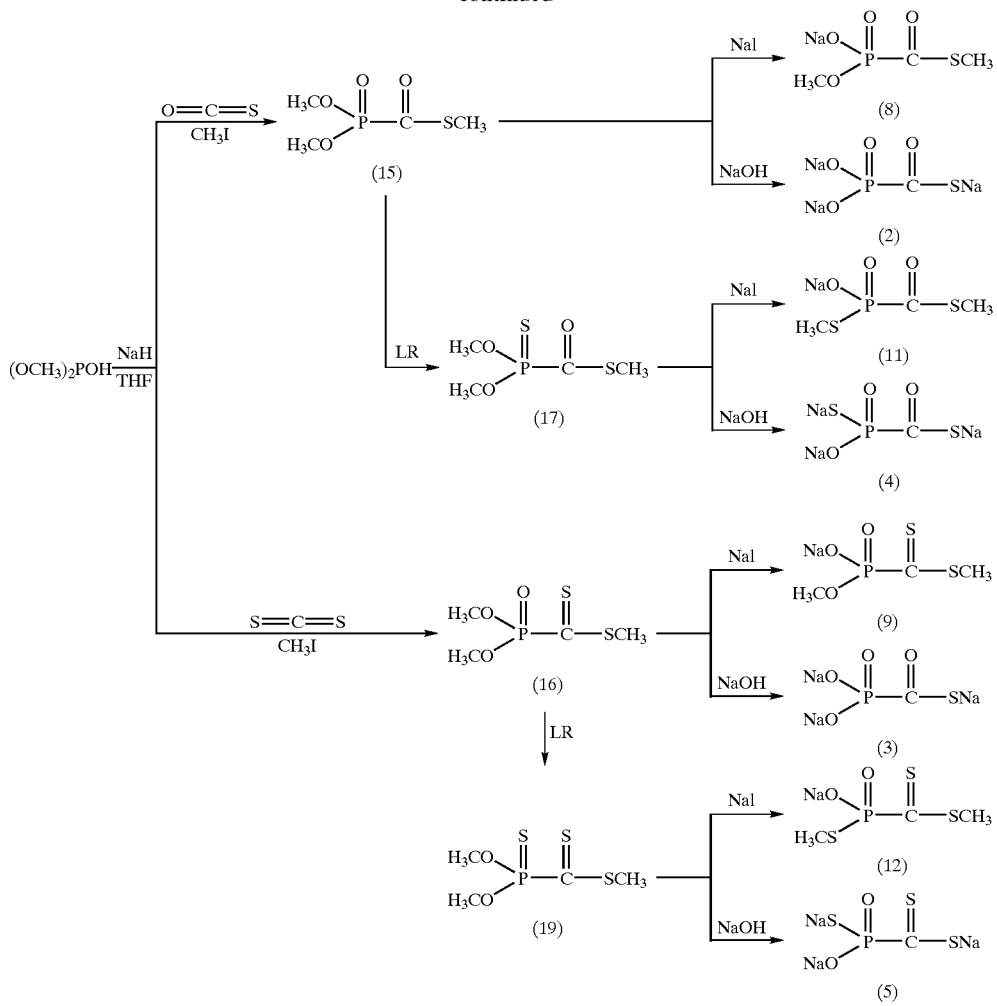

The unique biological activities of the sulfur containing PFA derivatives disclosed herein, and their corresponding classes, derive chiefly from two factors: 1) modification of their reactivity, cell transport, cell permeation, metabolism, and enzyme or membrane receptor site binding properties due to the different chemical and physical properties of sulfur relative to oxygen; and 2) potential in situ physiological conversion of S to O, creating the possibility of prodrugs for which the actual drug has one or more S converted to O after administration. Another factor is the modified properties of prodrugs or other analogues in which the sulfur-containing function is derivatized, e.g. as an ester, ether, etc., relative to metabolic activation in vivo.

It will be appreciated that simple experiments by those skilled in the art will readily eliminate those compounds that are not stable or are synthetically unattainable.

PFA Derivatives Conjugated with Polyalcohols

In accordance with this invention, PFA and TPFA is conjugated with polyalcohols. We postulate that such compounds can have enhanced membrane transport properties, and thus higher activity than the parent in vivo. Some 15 years ago, oral delivery of different classes of drugs was shown to be facilitated by incorporation of 1-O-alkyl, 1-O-acyl-sn-glycerol-phosphate moieties. See, Ryu, et al., *J. Med. Chem.* 25, 1322–1329 (1982). More recent examples of this approach have been given by M. Fuji, et al., *J. Org. Chem.*, 62, 6804 (1997) and by K. Hostetler, et al., *Antiviral Research*, 31, 59–67 (1996).

A PFA derivative conjugated with a polyalcohol moiety according to the present invention has the general formula:

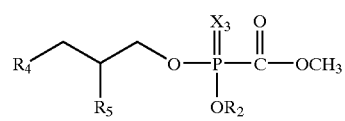

wherein $R_2$ is a hydrogen, cation, or $C_1$–$C_4$ alkyl, $R_4$ and $R_5$ are each independently $C_1$–$C_{16}$ alkoxy or $C_1$–$C_{16}$ alkyl acetate, and $X_3$ is sulfur or oxygen. Preferred versions of the polyalcohol conjugate include those where $R_2$ is sodium or methyl, and $R_4$ and $R_5$ are $C_{16}H_{33}O-$ or $CH_{15}H_{31}COO-$, and $X_3$ is oxygen.

The most preferred PFA derivatives of the present invention are those which act as antiviral compounds or their intermediates. Accordingly, a most preferred PFA derivative of the present invention is a polyalcohol conjugate having the following structure:

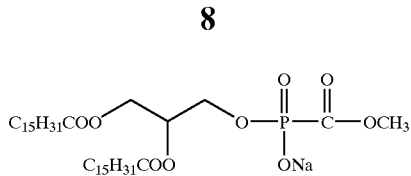

Our proposed synthetic routes are illustrated in Schemes 2 and 3 below.

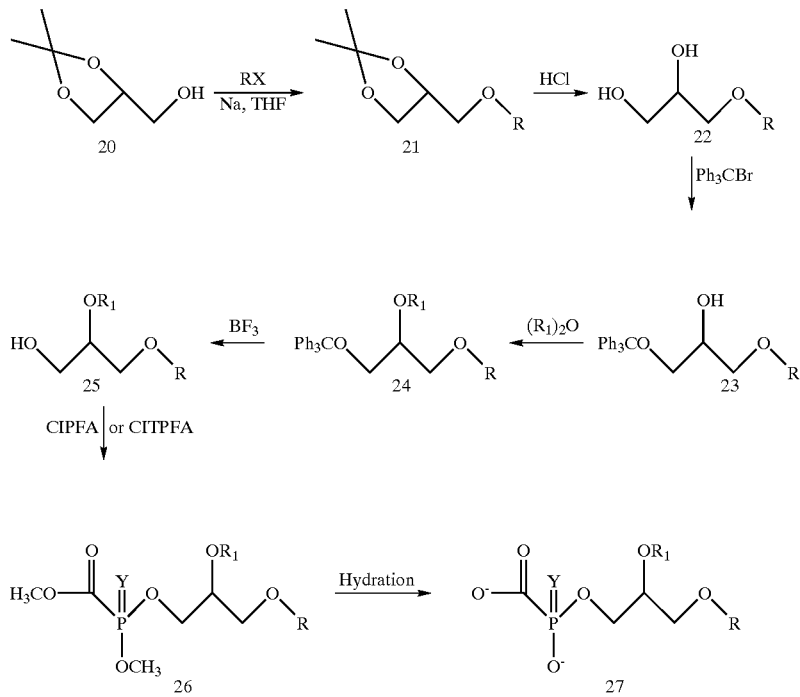

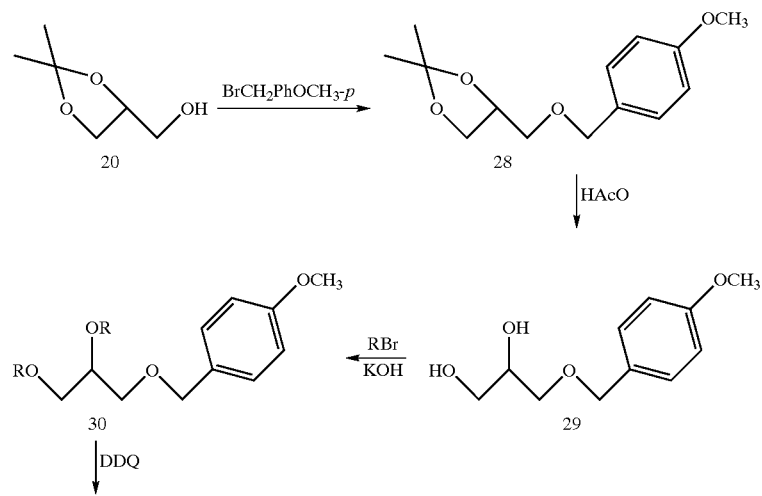

-continued

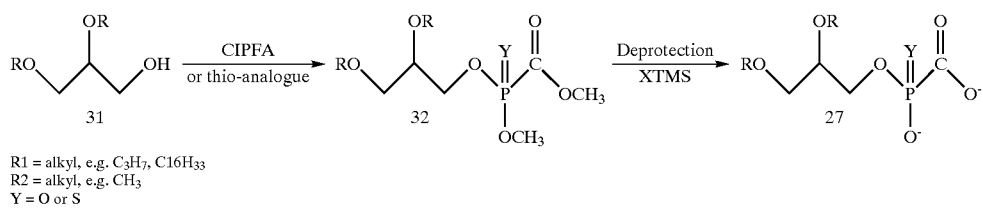

R1 = alkyl, e.g. C₃H₇, C16H33
R2 = alkyl, e.g. CH₃
Y = O or S

Lipophilic Phosphonocarboxylate Derivatives

While PFA is an excellent inhibitor of RT and DNA polymerases, its triple negative charge at physiological pH is an impediment to cellular uptake. Also, its in vivo clearance is very rapid because of its extremely hydrophilicity. Recent work has shown that the antiviral efficacy of PFA against both HIV-1 and CMV can be increased by coupling the phosphonate moiety to lipophilic group. [Hostetler, K. Y. et al., *Antiviral Res.* 31, 59–67 (1996); Rosowsky, A. et al, *J. Med. Chem* 40, 2482–2490 (1997)]).

In accordance with the present invention, a series of lipophilic PFA derivatives were prepared having the general formula

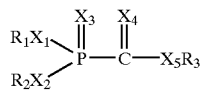

wherein $R_1$, $R_2$ and $R_3$ are either alkyl or cation, $X_1$, $X_2$, and $X_4$ are S or O, $X_2$ and $X_5$ are O, and one of either $R_1$ or $R_3$ is $C_3$–$C_{16}$ alkyl.

A preferred version of a lipohilic PFA derivative, which exhibited moderate to relatively high antiviral activity when tested in bioassay with HHV-8 has the following formula:

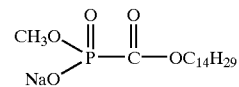

Synthesis of C-lipophilic ester PFA derivatives wherein the long chain is linked to PFA or TPFA via C-ester 35–40, are given in Scheme 4 and Scheme 5. These synthetic pathways modify PFA or TPFA to resemble fatty acids by coupling to lipophilic fatty alcohols. Examples of P-lipophilic TPFA ester derivatives 42–50 are given in Scheme 6. In the examples below, the lipophile is a $C_7$, $C_8$, $C_{14}$, or $C_{16}$ alkyl group, or alternatively, a cis-11-$C_{16}$ alkenyl group.

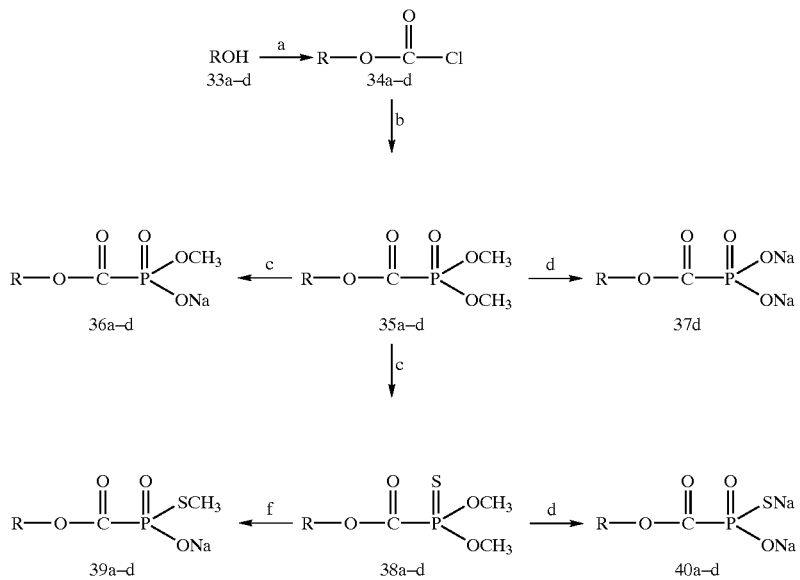

Scheme 4 a. (Cl₃CO)₂CO/Et₃N;
b. P(OCH₃)₃;
c. NaI/acetone;
d. Na/CH₃OH;
e. LR/toluene;
f. NaI/acetone Scheme 5

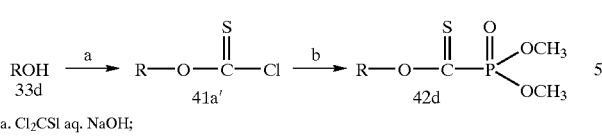

a. Cl₂CSI aq. NaOH;
b. P(OCH₃)₃

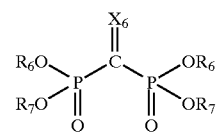

Scheme 6

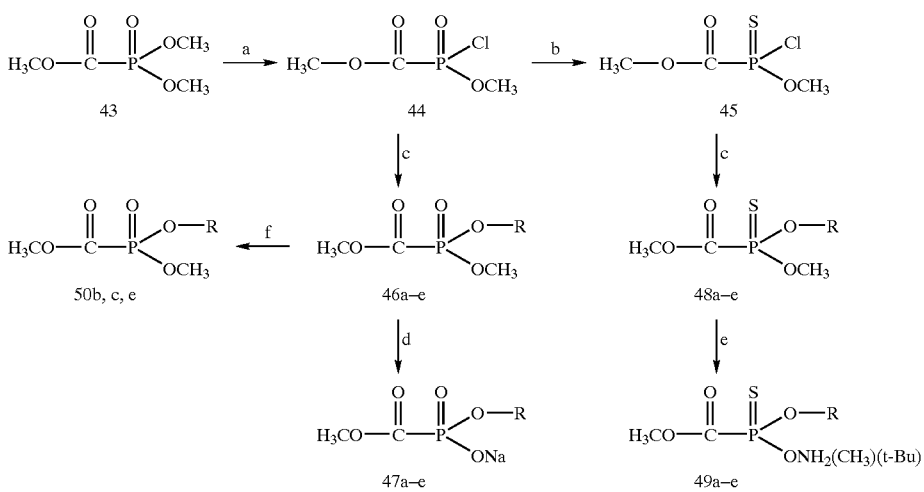

a. PCl₅/CCl₄;
b. LR/toluene;
c. ROH/ether/pyridine;
d. NaI/acetone;
e. t-BuNH₂;
f. aq NaOH Demethylation of P-lipophilic TPFA ester derivatives with sodium iodide resulted in an (RO)P=S→(RS)P=O rearrangement and loss of the long chain. Based on NMR data, the $S_N2$ mechanism for this rearrangement was suggested, as in Scheme 7. An (RO)P=S→(RS)P=O rearrangement during the dealkylation of TPFA methyl esters can be avoided by using t-butylamine, giving products 49.

Scheme 7

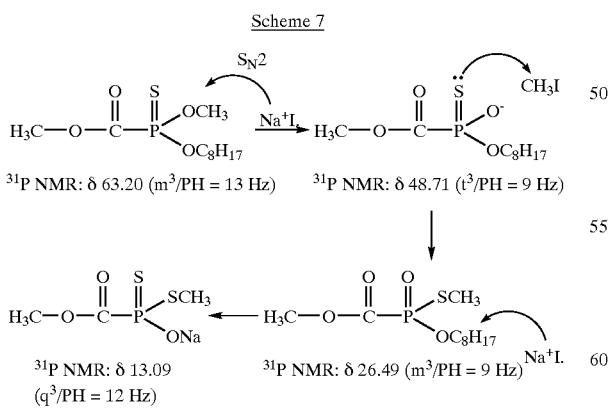

Bisphosphonic Acid Derivatives

Bisphosphonic acid derivatives, for use in the methods and compositions of the present invention, have the following general formulas:

wherein $R_6$ and $R_7$ are each independently cation or $C_1$ to $C_{16}$ alkyl and $X_6$ is oxygen, $CH_2$, or $NNHX_7$; wherein $X_7$ is aryl; or

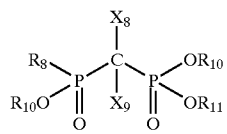

wherein $R_8$ is aryl or $OR_9$, $R_9$ is cation or $C_1$ to $C_{16}$ alkyl, $R_{10}$ is cation, $C_1$ to $C_{16}$ alkyl, or pyridine.

Preferred versions of the compositions and methods of the present invention include the following disphosphonic acid derivatives, which exhibited moderate to relatively high antiviral activity when tested in a bioassay with HHV-8:

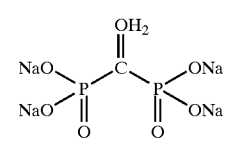

-continued

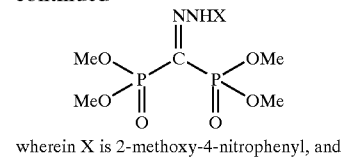

wherein X is 2-methoxy-4-nitrophenyl, and

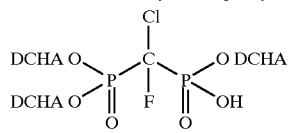

These bisphosphonic acid derivatives are known compounds and therefore, the compounds as such and their chemical synthesis are not a part of the present invention. However, the present invention discloses for the first time the use of these derivatives as effective antiviral compounds in pharmaceutical compositions and methods for treating viral infections, such as HHV-8.

The synthesis of a number of bisphosphonic acid derivatives have been described in the literature. See, e.g. Peng, Z-Y et al., Biochem. Pharmacol. 49, 105–113(1995).

Phosphonoacetic Acid Derivatives

Phosphonoacetic acid derivatives, for use in the methods and compositions of the present invention, have the following general formulas:

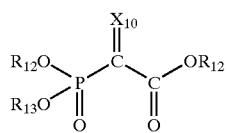

IV wherein $R_{12}$ is cation or $C_1$ to $C_{16}$ alkyl, $R_{13}$ is cation, hydrogen, or $C_1$ to $C_{16}$ alkyl, $X_{10}$ is oxygen or $NNHX_{11}$, and $X_{11}$ is aryl; or

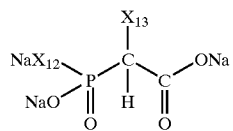

V

Wherein $X_{12}$ sulfur or oxygen, and $X_{13}$ are hydrogen or halogen.

A preferred version of the compositions and methods of the present invention includes the following phosphonoacetic acid derivative, which exhibited moderate to relatively high antiviral activity when tested in a bioassay with HHV-8:

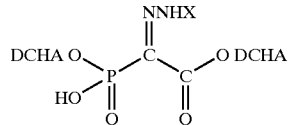

wherein X is 2,4-dinitrophenyl.

These phosphonoacetic acid derivatives are known compounds and therefore, the compounds as such and their chemical synthesis are not a part of the present invention. However, the present invention discloses for the first time the use these derivatives as effective antiviral compounds in pharmaceutical compositions and methods for treating viral infections.

The synthesis of a number of bisphosphonic acid derivatives have been described in the literature. See, e.g., McKenna, C. E., et al., Phosphorus and Sulfur, 37, 1–12 (1988).

Antiviral Activity of Pyrophosphate Analogues

"Antiviral" activity is generally determined by infecting susceptible tissue culture cells capable of harboring the virus to be tested and incubating for a period of time. The infected tissue culture is then treated with the test compound or composition. The degree of antiviral activity is measured by comparing the quantity of virus present in chemically treated tissue cultures with untreated tissue cultures.

Of particular interest are antiviral compounds effective against infections by human herpes viruses, which are among the most common and easily transmitted viral conditions. Numerous distinct viruses have been identified, as shown in the Table I below, including HSV, VZV, CMV, EBV, etc. Human herpesvirus (HHV)-8 is a novel member of the lymphotropic human herpesvirus family. Having a high degree of homology with EBV and Herpesvirus saimiri of the Gammaherpesvirinae subfamily, they have been considered a new member of the subfamily.

TABLE I

Significant herpes viruses affecting man

| Subfamily | Virus | Abbreviation |
| --- | --- | --- |
| Alphaherpesvirinae | Herpes simplex virus type 1 | HSV-1 |
|  | Herpes simplex virus type 2 | HSV-2 |
|  | Varicella zoster virus | VZV |
| Betaherpesvirinae | Cytomegalovirus | CMV |
|  | Human herpesvirus type 6 | HHV-6 |
|  | Human herpesvirus type 7 | HHV-7 |
| Gammaherpesvirinae | Epstain-Barr virus | EBV |
|  | Human herpesvirus type 8 | HHV-8 |

Positive HHV-8 serology correlates with risk of Kaposi's Sarcoma, which is the most frequent neoplasm afflicting persons with AIDS. HIV infection is a substantial risk factor in the development of KS; persons with AIDS manifest the disease at a rate 20,000-fold greater than that in the general population. HHV-8 has also been detected in primary effusion lymphomas [Cesarman, E. et al., N. Engl. J. Med. 332, 1186–1191 (1995)], Castleman's disease [Soulier, J. et al., Blood 86, 1276–1280 (1995)], and multiple myeloma [Rettig, M. B. et al., Science 276, 1851–1854 (1997)] and reported anecdotally in cases of angioimmunoblastic lymphdenopathy and germinal-center hyperplasia [Luppi, M. et al., Blood 87, 3903–3909 (1996)].

Accordingly, members of each class of pyrophosphate analogues described herein were evaluated for their ability to inhibit HHV-8. As described in greater detail in the examples below, Shoemaker et al. ("Characterization of a quantitative PCR-based assay for agents active against human herpesvirus 8"; 3rd National AIDS Malignancy Conference, May 26–28, 1999, Bethesda, Md.) have developed a quantitative PCR-based assay for agents active against HHV-8. This assay is derived from the assay described by Keddes and Ganem [J. Clin. Invest. 99, 2082–2086 (1997)] utilizing the BCBL-1 chronically infected body cavity lymphoma cell line. Culturing these cells in the presence of phobol ester induces a lytic infection cycle, resulting in the release of viral particles into the medium. Compound efficacy in this proposed assay was determined using the Taqman PCR technology, and compound toxicity to host cells was assessed using an XTT-tetrazolium assay.

Although compounds and compositions that have antiviral activity against one virus or even a class of viruses, do not necessarily have antiviral activity against other viruses, even within the same class, PFA is unique in exhibiting a broad spectrum of activity against a variety of both RNA and DNA viruses. Thus, although there is a high degree of unpredictability in both the mode of activity and virus selectivity for most antiviral compositions, the pyrophosphate analogues of the present invention are expected to provide a broad spectrum of antiviral activity much like PFA.

Compositions and Method of Use

The antiviral compounds of the present invention may be formulated for oral or parenteral use in a conventional manner using known pharmaceutical carriers and excipients, and they may be presented in unit dosage form or in multiple dose containers. The compositions may be in the form of tablets, capsules, solutions, suspensions or emulsions. These compounds may also be formulated as suppositories utilizing conventional suppository bases such as cocoa butter or other fatty materials. The compounds may, if desired, be administered in combination with other antiviral agents.

When provided in unit dosage forms, the antiviral compositions may contain from about 0.1 to about 100 mg/kg/dose of the active ingredient, however the dosage of the pyrophosphate analogues is dependent on such factors as the weight and age of the patient, as well as the particular nature and severity of the disease, and is within the discretion of the physician. The dosage for adult human treatment may also vary depending on the frequency and route of administration.

The pyrophosphate analogues and compositions of the present invention having antiviral activity are generally used in a method to treat patients having an existing viral infection. The composition can be administered in a unit dosage form as described above. A therapeutically effective amount of the antiviral compositions, to be used in accordance with this invention, can be optimized by methods known in the art. Dose frequency can be determined by measuring half-life according to standard techniques and preferably will be about 1–3 times daily, although less frequent administration may have a positive effect. Treatment is continued until no further clinical improvement is observed, e.g., by viral load or other clinical measures, and preferably longer.

EXAMPLES

General Experimental Protocols

Solvents for reactions were purified as follows: THF was distilled from sodium and benzophenone ketyl, toluene was distilled from $CaH_2$, and acetone was dried with molecular sieve. Solvents for column chromatography or Thin Layer Chromatography (TLC) were not pretreated. The end points of all reactions were checked using TLC or NMR except noted. Monosodium salts and trisodium salts were dried in a vacuum, and all the products were stored at 4° C.

All solvents and reagents were of Analytical Reagent (AR) grade quality, purchased from Sigma-Aldrich, Inc., without further purification except where noted. Nuclear Magnetic Resonance (NMR) spectra were recorded on $CDCl_3$ solutions for triesters and on $D_2O$ for monosodium salts and trisodium salts. $^1H$ and $^{13}C$ spectra were recorded on Bruker AC250 MHz or AM360 MHz spectrometers, in $CDCl_3$. $^1H$ chemical shifts are referenced to $CHCl_3$ ($\delta 7.24$). $^{13}C$ chemical shifts were referenced to: $CDCl_3$ ($\delta 77.0$); $D_2O$ HDO ($\delta 4.63$); and $C_6D_6$ ($\delta 128$). $^{31}P$ spectra were recorded on the 360 MHz instrument. $^{31}P$ NMR chemical shifts are referenced to external 85% $H_3PO_4$. Chemical shifts are reported in ppm (s=singlet, d=doublet, t-triplet, q=quartet, m=multiplet). High Resolution Mass Spectra (HRMS) determinations were performed at UC Riverside.

Example 1

Synthetic Procedures for Thio-Analogues:
Trimethyl Esters
S-Methyl(Dimethylphosphinyl)thioformate (15)

S-Methyl(Dimethylphosphinyl)thioformate (15), was prepared by a previously published method (Kovalenko, et al., *Russian Journal of General Chemistry*, 64 (10) Part 1, 1456, (1994)). A solution of 1.00 g (9 mmol) of S-methyl chlorothioformate in 5 mL of dry toluene was added over 10 min to a solution of 1.12 g (9 mmol) of trimethyl phosphite in 10 mL of dry toluene. The mixture was stirred and maintained below 30° C. for 2 h. Toluene was removed by rotary evaporation under reduced pressure, and the resulting residue was distilled in vacuo, giving 0.72 g of a colorless oil, b.p.: 78–80° C./20µ. The yield of product was about 55.6%.

S-Methyl(Dimethylphosphinyl)thioformate (15), also was prepared by a previously published method (Grisley, D. W., Jr., *J. Org. Chem.* 26:2544, (1961)). 11.0 g (0.1 mole) of dimethyl phosphite was added dropwise to a stirred solution of 2.4 g (0.1 mole) of sodium hydride in 50 mL of dry THF at 25–30° C. under $N_2$. The mixture was stirred and refluxed until $H_2$ evolution ceased. The mixture was then cooled to 6° C. and carbonyl sulfide gas was passed into the mixture until 6.7 g (0.11 mole) was absorbed. Methyl iodide (14.2 g, 0.1 mole) was then added at 5° C. over 15 min. The mixture was poured into 350 ml of ice-water and extracted with ether (3×100 mL). The ether layers were combined, dried with anhydrous magnesium sulfate, filtered, evaporated to remove ether and distilled in vacuo. The fraction boiling between 87–89° C./100µ was collected, 5.9 g, Y=32.1%. $^1H$ NMR: $\delta$(ppm) 3.87 (d, 6H, $^3J_{HP}$=11 Hz, $POCH_3$), 2.40 (d, 3H, $^4J_{HP}$=1 Hz, $CSCH_3$); $^{13}C$ NMR: $\delta$(ppm) 197.7 (d, $^1J_{CP}$=208 Hz, $\underline{C}O$), 54.6 (d, $^2J_{CP}$=7 Hz, $POCH_3$), 11.0 (d, $^3J_{CP}$=4 Hz, $CSCH_3$); $^{31}P$ NMR: $\delta$(ppm) −1.44 (m, $^3J_{PH}$=11 Hz); $^{31}P$ NMR {H}: $\delta$(ppm) −1.44 (s); HRMS: 185.0041 ($MH^+$, Found); 185.0037 ($MH^+$, Calcd).

Methyl(Dimethoxyphosphinyl)thioformate (14)

O-methyl chlorothioformate was prepared as follows: To a stirred solution of 40 g sodium hydroxide, 150 mL of water and 200 mL of methanol, cooled by means of an ice-bath, carbon disulfide (24 mL) was added dropwise over a 1 hour period. The mixture was treated with 0.1 g of KI and chlorine gas passed in until the purple color of free iodine was observed (end-point). The iodine color was discharged with 10% $NaHCO_3$. The mixture was washed with water (3×50 mL) and dried with $CaCl_2$. After filtration, a yellowish-green crude oil was obtained. $^1H$ NMR: $\delta$(ppm) 4.22. [See, Irwin B. Douglass and Glenn H. Warner, *J.Am.Chem.Soc.*, 78:6070 (1956)].

While cooled externally with cold water, 34 g of the crude oil described above was treated with 9 g of chlorine. The temperature should not exceed 30° C. to avoid over-chlorination. The mixture was heated slowly, then fractionated. The fraction boiling at 84–86° C./760 mm was collected, giving 12.7 g of O-methyl chlorothioformate, Y=72%. $^1H$ NMR: $\delta$(ppm) 4.16. [See, Dieter Martin and Wolfgang Mocke, *Chemishe Berichte*, 98 (7), 2059 (1965).[4]] A solution of 0.55 g (5 mmol) of O-methyl chlorothioformate in 8 mL of dry toluene was added over 10 min to a solution of 0.62 g (5 mmol) trimethyl phosphite in 15 mL of dry toluene under $N_2$. The mixture was stirred and left for 2 hr at room temperature. The solvent was rotary-evaporated, and the residue distilled in vacuo, giving 0.52 g of a yellow oil, 80–81° C./100μ, Y=56.5%. $^1$H NMR: δ(ppm) 4.18 (d, 3H, $^4J_{HP}$=2 Hz, COCH$_3$), 3.87 (d, 6H, $^3J_{HP}$=11 Hz POCH$_3$); $^{13}$C NMR: δ1 (ppm)2.5 (d, $^1J_{CP}$=223 Hz, PC), 59.1 (d, $^2J_{CP}$=8 Hz, POCH$_3$), 54.8 (d, $^3J_{CP}$=6 Hz, COCH 3); 31P NMR {H}: δ(ppm) −1.14 (s); $^{31}$P NMR: δ (ppm) −1.14 (m, $^3J_{PH}$=11 Hz); HRMS: 185.0031 (MH$^+$, Found); 185.0037 (MH$^+$, Calcd).

Methyl(Dimethoxyphosphinyl)dithioformate (16)

Dimethyl phosphite (11.0 g 0.1 mol) was added dropwise to a stirred solution of 2.4 g (0.1 mole) of sodium hydride in 50 mL of dry THF at 25–30° C. under N$_2$. The mixture was stirred under reflux until H$_2$ evolution ceased. It was then cooled to 6° C. and was added with stirring to carbon disulfide (38 g, 0.5 mol) at 2–8° C. over 15 min. Methyl iodide (14.2 g 0.1 mol) was then added at 5° C. over 15 min. The mixture was quenched with 350 mL of ice-water and extracted with ether (100 mL×3). The ether layers were combined, dried with anhydrous magnesium sulfate, filtered, evaporated to remove ether and distilled in vacuo. The fraction boiling between 92–94° C./50μ was collected, 6.5 g, Y=32.5%. (Put footnote 2 here) $^1$H NMR: δ(ppm) 3.85 (d, 6H, $^3J_{HP}$=10 Hz, POCH$_3$), 2.69 (d, 3H, J$_{HP}$=1 Hz CSCH$_3$); $^{13}$C NMR: δ(ppm) 228(d, $^1J_{CP}$=175 Hz, CS), 54.5 (d, $^2J_{CP}$=6 Hz, POCH$_3$), 10.9 (s, CSCH$_3$); $^{31}$P NMR {H}: δ(ppm) 0.30(s); $^{31}$P NMR: δ(ppm) 0.30 (m, $^3J_{PH}$=11 Hz); HRMS: 199.9732 (Found); 199.9731 (Calcd).

Methyl(Dimethoxythiophosphinyl)formate (13)

The process of Methyl(Dimethoxyphosphinyl)dithioformate (16) was repeated for Methyl(Dimethoxythiophosphinyl)formate (13), with the following results: $^1$H NMR: δ(ppm) 3.89 (s, 3H, COCH$_3$), 3.79 (d, 6H, $^3J_{PH}$=13 Hz POCH 3); $^{13}$C NMR: δ(ppm) 167.5 (d, $^1J_{CP}$=227 Hz, CO), 54.5 (d, $^2J_{CP}$=6 Hz, POCH3), 52.9 (s, COCH$_3$); $^{31}$P NMR {$^1$H}: □(ppm) 64.9. This is a compound previously described in McKenna's U.S. Pat. Nos. 5,072,032 and 5,183,812.

S-Methyl(Dimethoxythiophosphinyl)thioformate (17)

The process of Methyl(Dimethoxyphosphinyl)dithioformate (16) was repeated for S-Methyl(Dimethoxythiophosphinyl)thioformate (17), with the following results: $^1$H NMR: δ(ppm) 3.85 (d, $^3J_{HP}$=12 Hz, 6H, POCH$_3$), 2.39 (d, $^3J_{HP}$=12 Hz, 3H, CSCH$_3$); $^{13}$C NMR: δ(ppm) 198.4 (d, $^1J_{CP}$=163 Hz, CS), 54.6 (d, $^2J_{CP}$=6 Hz, POCH$_3$), 11.6 (s, CSCH$_3$); $^{31}$P NMR: □δ(ppm) 68.0 ($^3J_{PH}$=12 Hz); HRMS: 200.9827 (MH$^+$, Found); 200.9809 (MH$^+$, Calcd).

Methyl(Dimethoxythiophosphinyl)thioformate (18)

The process of Methyl(Dimethoxyphosphinyl)dithioformate (16) was repeated for Methyl(Dimethoxythiophosphinyl)thioformate (18), with the following results: NMR: $^1$H, δ(ppm) 4.19 (s, 3H, COCH$_3$), 3.87 (d, 6H, $^3J_{PH}$=11 Hz POCH$_3$); $^{13}$C NMR: δ(ppm) 214.5 (d, $^1J_{CP}$=180 Hz, CS), 59.5 (d, $^2J_{CP}$=9 Hz, POCH$_3$), 55.0 (d, J$_{CP}$=7 Hz, COCH$_3$); $^{31}$p NMR {$^1$H}: δ(ppm) 67.2; HRMS: 200.9815 (MH$^+$, Found); 200.9809 (MH$^+$, Calcd).

(Dimethoxythiophosphinyl)dithioformate (19)

The process of Methyl(Dimethoxyphosphinyl)dithioformate (16) was repeated for Methyl(Dimethoxythiophosphinyl)dithioformate (19), with the following results: $^1$H NMR: δ(ppm) 3.89 (d, 6H, $^3J_{HP}$=13 Hz, POCH$_3$), 2.67 (d, 3H, $^4J_{HP}$=4 Hz, CSCH$_3$); $^{13}$C NMR: δ(ppm) 231.0 (d, $^1J_{CP}$=136 Hz, CS), 55.0 (d, $^2J_{CP}$=7 Hz, POCH$_3$), 19.8 (d, $^3J_{CP}$=3 Hz, CSCH$_3$); $^{31}$P NMR {H}: δ(ppm) 70.0; $^{31}$P NMR: δ(ppm) 70.0 (m, $^3J_{PH}$=11 Hz); HRMS: 216.9581 (Found); 216.9581 (Calcd); Microanalysis: C%; 22.22 (Calcd); 22.24 (Found); H%; 4.19 (Calcd); 4.25 (Found).

General Procedure (using Lawesson's Reagent, LR)

LR (7.2 g, 17.8 mmol) was weighed out in a Dry Box and suspended in 100 mL of dry toluene. Trimethyl phosphonoformate, (11.4 mmol) in 10 mL of dry toluene was added. The mixture was refluxed for 6 h. The solid by-product was filtered, and toluene removed in vacuo. The residue was extracted with 40 mL of dry hexane, and the extract filtered, evaporated and distilled in vacuo to give the desired product. The preceding general procedure was followed wherein: (1) the Me$_3$PTLFA was substituted for trimethyl phosphonoformate; (2) the Me$_3$PTNFA was substituted for trimethyl phosphonoformate; and (3) the Me$_3$PDTFA was substituted for trimethyl phosphonoformate.

Example 2

Synthetic Procedures for Thio-Analogues: Mono-P Ester Monosodium Salts

General Procedure

In a 20 mL flask, 0.5 mmol of the corresponding trimethyl ester was dissolved in 15 mL of dry acetone. NaI (75 mg, 0.5 mmol) dissolved in 2 mL acetone was added, and the mixture was refluxed for 2 h. The mixture was then cooled, filtered, and the precipitate washed with dry acetone until the wash was negative to AgNO$_3$. The final product was dried in a vacuum oven.

NaTPFA (6)

The preceding general procedure was followed wherein NaTPFA (6), was synthesized. $^1$H NMR: δ(ppm) 3.68 (d, 3H, $^3J_{HP}$=1 Hz, POCH$_3$); 2.12 (d, 3H, $^3J_{HP}$=13 Hz, SCH$_3$); $^{13}$C NMR: δ(ppm) 171.0 (d, $^1J_{CP}$=150 Hz, CO), 50.81 (POCH$_3$); 10.43 (d, $^2J_{CP}$=4 Hz, SCH$_3$); $^{31}$P NMR: δ(ppm) 18.1 (q, $^3J_{PH}$=10 Hz); Microanalysis: C%, 18.76 (Calcd); 19.27 (Found); H%, 3.15 (Calcd); 3.06 (Found); S%, 16.69 (Calcd); 17.08 (Found).

NaPTLFA (8)

The preceding general procedure was followed wherein NaPTLFA (8), was synthesized. $^1$H NMR: δ(ppm) 3.48 (d, 3H, $^3J_{HP}$=11 Hz, POCH$_3$), 2.22 (s, 3H, CSCH$_3$) $^{13}$C NMR: δ(ppm) 207.4 (d, $^1J_{CP}$=190, CO); 53.3 (d, $^2J_{CP}$=6 Hz, POCH$_3$); 10.1 (s, SCH$_3$); $^{31}$P NMR: δ(ppm) 0.76 (q, $^3J_{PH}$=11 Hz).

NaPTNFA (7)

The preceding general procedure was followed wherein NaPTNFA (7), was synthesized. $^1$H NMR: δ(ppm) 4.01 (d, 3H, $^4J_{HP}$=1 Hz, COCH$_3$), 3.47 (d, 3H, $^3J_{HP}$=11 Hz, POCH$_3$); $^{13}$C, δ(ppm) 222.1 (d, $^1J_{CP}$=200 Hzs, CS); 58.9 (d, $^2J_{CP}$=8 Hz, POCH$_3$); 51.8 (d, $^3J_{CP}$=4 Hz OCH$_3$); $^{31}$P, δ(ppm) 0.26 (q, $^3J_{PH}$=11 Hz).

The preceding general procedure was followed wherein NaPDTFA (9), was synthesized. NMR: $^1$H, δ(ppm) 3.46 (d, 3H, $^3J_{HP}$=12 Hz, POCH$_3$), 2.52 (d, 3H, $^4J_{HP}$=1 Hz, CSCH$_3$); $^{13}$C, δ(ppm) 239.0 (d, $^1J_{CP}$=150, CS); 53.3 (d, $^2J_{CP}$=6 Hz, POCH$_3$); 18.9 (s, SCH3); $^{31}$P, δ(ppm) 2.25 (q, $^3J_{PH}$=11 Hz).

NaTPTLFA (11)

The preceding general procedure was followed wherein NaTPTLFA (11), was synthesized. NMR: $^1$H, δ(ppm) 2.20 (s, 3H, CSCH$_3$), 2.05 (d, 3H, $^3$ J$_{HP}$=12 Hz, PSCH$_3$); $^{13}$C, δ(ppm) 204.2 (d, $^1J_{CP}$=140, CO); 12.0 (d, $^2J_{CP}$=4 Hz, PSCH$_3$); 10.5 (s, SCH$_3$); $^{31}$P, δ(ppm) 22.2 (q, $^3J_{PH}$=12 Hz).

Example 3

Synthesis of Polyhydroxy Derivatives

Isopropylidene Glycerol, Scheme I2 Compound 20

Freshly distilled glycerol (10 g, 0.11 mole) was shaken until dissolved with 65 mL of dry acetone containing 1 g of TsOH. After 24 hr. the solution was neutralized first with PbCO$_3$ and afterwards with Ag$_2$CO$_3$, warmed with charcoal, and shaken with a large excess of CaCl$_2$ overnight. The supernatant liquid was then filtered. The solvent was removed by rotary evaporation, and the product fractionated under diminished pressure, giving 9.5 g of the main fraction (b.p. 105–106° C./25 mm) Y=65.4%. NMR: $^1$H, δ(ppm) 4.14–4.16 (m, 1H, CH), 3.65–4.0 (qxd, 2H, CH$_2$), 3.57 (m, 2H, CH$_2$OH), 2.05 (sb. 1H,OH), 1.40, 1.33 (CH$_3$); $^{13}$C, δ(ppm) 109.4 (COO), 76.1 (CH), 65.7 (CH$_2$O), 62.8 (CH$_2$OH), 26.6, 25.2 (CH$_3$).

Propyl Isopropylideneglyceryl Ether, Scheme 2 Compound 21a

To a stirred solution of the protected glycerol (1.3 g, 10 mmol) in dry THF (20 mL) was added NaH (0.6 g, 25 mmol) portionwise at 0° C. After the reaction mixture was stirred for 30 min, 1-bromopropane (3.0 g, 25 mmol) was added. The mixture was stirred at r.t. Once the reaction was completed, 2 mL of methanol was added at 0° C. to destroy the excess of NaH. The solvent was evaporated under vacuum. (b.p. 40–42° C./50μ) The residue was extracted with ethyl acetate. The extract was washed with water. After the dried solvent was removed, 0.86 g of a yellow oil obtained (Y=49%). NMR: $^1$H, δ(ppm) 4.20–4.17 (m, 1H, CH), 3.65–4.0 (qxd, 2H, CH$_2$), 3.33–3.42 (m, 4H, CH$_2$OCH$_2$), 1.51 (m 2H, CH$_2$CH$_2$CH$_3$), 1.27, 1.33 (s, 6H, CH$_3$CCH$_3$), 0.82 (t, 3H, CH$_3$); $^{13}$C, δ(ppm) 109.1 (COO), 74.6 (CHCH$_2$O), 73.2 (CH), 71.6 (CCH$_2$O), 66.7 (OCH2CH$_2$CH$_3$), 25.2, 26.6 (CH$_3$CCH$_3$), 22.6 (OCH$_2$CH$_2$CH$_3$), 10.3 (CH$_2$CH$_2$CH$_3$).

Propyl Glyceryl Ether, Scheme 2 Compound 22a

HCl (1 M, 2 mL) was added to a solution of 0.80 g (4.6 mmol) propyl isopropylidene ether in 3.0 mL of methanol and the reaction was stirred for 2 hr at room temperature. The reaction mixture was extracted with 3×20 mL of ethyl ether, and the combined ether extracts were dried over sodium sulfate. After removal of the solvent, the residue weighed 0.51 g (Y=83.6%). NMR: $^1$H, δ(ppm) 5.1 (m, 1H, CH), 3.37–3.68 (m, 6H, CH$_2$), 2.05 (sb, 2H, OH), 1.56 (2H, OCH$_2$CH$_2$), 0.88 (t, 3H, CH$_2$CH$_2$CH$_3$); $^{13}$C, δ(ppm) 73.3 (CH), 72.4 (CH$_2$OH), 70.5 (CH$_2$OCH$_2$), 64.2 (OCH$_2$CH$_2$), 62.7 (OCH$_2$CH$_2$), 10.4 (CH$_3$).

Benzyl Glyceryl Ether, Scheme 2 Compound 22b, Alternative

As an alternative procedure to a stirred solution of the protected glycerol (6.7 g, 0.05 mole) in dry THF (100 mL) was added NaH (1.8 g, 0.075 mole) portionwise at 0° C. The reaction mixture was refluxed for 1.5 h, and benzyl bromide (10.3 g, 0.06 mole) was added. The mixture was stirred at room temperature. Once the reaction was completed, 2 mL of methanol was added at 0° C. to destroy the excess of NaH. The reaction mixture was extracted with 3×50 mL of ethyl ether, and the combined ether layers dried over sodium sulfate. After solvent removal, the residue of (11.9 g, Y=61%). was combined with 60 mL of 10% acetic acid, then heated (oil bath, 100° C.), until the original emulsion disappeared (about 0.5 h), After concentration, the residue was distilled in vacuo, giving 8.1 g (b.p.116–118° C./50μ) (Y=89%).

Hexadecanyl Isopropylidene Glyceryl Ether, Scheme 2 Compound 21b, Alternative

As another alternative procedure, to prepare Scheme II, Compound 2, NaH (0.6 g, 0.025 mole) was added to 4 mL of THF containing 1.3 g (0.01 mole) of isopropylidene glycerol at 0° C. Gas was generated. After ~0.5 h, 3.0 g (0.01 mole) of hexadecanyl bromide was added dropwise. The reaction mixture was stirred for 2 h at room temperature. Methanol was added at 0° C. to destroy excess sodium hydride. The mixture was filtered, and the filtrate evaporated. The residue was extracted with 2×60 mL ethyl ether. The extract was washed with brine and water and dried over Na$_2$SO$_4$. After concentration, 2.36 g of crude product was obtained (Y=59%). NMR: $^1$H, δ(ppm) 4.24 (m, 1H, CH), 4.04–3.70 (qxd, 2H, CH$_2$), 3.44 (m, 4H, CH$_2$OCH$_2$), 1.40 (q, 2H, OCH$_2$CH$_2$, $^3$J$_{HH}$=7 Hz), 1.33 (d, 6H, CCH$_3$), 1.22 (s, 28H, CH$_2$), 0.85 (t, 3H, CH$_3$, $^3$J$_{HH}$=7 Hz).

Hexadecanyl Glyceryl Ether, Scheme 2 Compound 22c, Alternative

Hexadecanyl isopropylidene glyceryl ether (150 mg, 0.4 mmol), 4 mg of TsOH.H$_2$O and 20 mL of methanol were stirred at 0° C. overnight. Removal of the solvent gave 110 mg of a white solid, which was dissolved in 1 mL of chloroform, filtered and concentrated, and dried (vacuum oven) leaving 105 mg of product (m.p. 54–56° C.). Pure product was obtained by recrystallization from ether, m.p. 62–64° C. NMR: $^1$H, δ(ppm) 4.93 (m, 1H, CH), 3.83–3.66 (qxd, 2H, CH$_2$OH), 3.49–3.41 (m, 4H, CH$_2$OCH$_2$), 2.80 (s,b, 2H, OH), 1.54 (m, 2H, CH$_2$CH$_3$), 1.23 (s, 26H, CH$_2$), 0.85 (t, 3H, $^3$J$_{HH}$=7 Hz, CH$_3$); $^{13}$C, δ(ppm) 72.4 (CHOH), 71.8, 70.5 (CH$_2$OCH$_2$), 64.0 (CH$_2$OH), 31.9, 29.7, 29.6, 29.5, 29.4, 29.3, 29.1, 29.0, 28.9, 22.7 (CH$_2$), 14.1 (CH$_3$); HRMS: 317.3047 (Found); 317.4056 (Calcd); Microanalysis: C%, 72.12 (Found); 72.10 (Calcd); H%, 13.05 (Found); 12.74 (Calcd).

Synthesis of Scheme 2 Compound 24

The Scheme 2 compound 23 (0.75 g, 1.3 mmole), 3 mL of pyridine, and 1 mL of acetic anhydride were stirred for 45 h at room temperature. 2 g of ice was added to the reaction mixture. 1.5 mL of chloroform was added to the mixture. The separated oil layer was then washed with 10% NaHCO$_3$ and water. The oil layer was rotary-evaporated after drying over MgSO$_4$. The residue was co-evaporated with 15 mL of toluene. 0.72 g of crude product was obtained. Purification was carried out by flash column chromatography, petroleum and ether, 7:3 as eluting agent giving 0.53 g (Y=67%) of pure compound. After standing, the product solidified, m.p. 43–44° C., NMR: $^1$H, δ(ppm) 7.40–7.18 (m, 15H, Ph—H), 5.15 (m, 1H, CH), 3.62–3.16 (m, 6H, OCH$_2$), 2.05(s, 3H, COCH$_3$), 1.48–1.21 (m, 28H, CH$_2$), 0.84 (t, 3H, $^3$J$_{HH}$=7.0 Hz CH$_3$); $^{13}$C, δ(ppm) 170.5(C=O), 143.8, 129.0, 128.6, 127.2(Ph—C), 86.5 (cph$_3$), 71.5 (CH), 69.4, 62.5, 61.0 (OCH$_2$), 31.9, 29.7, 26.0, 22.7 (m, CH$_2$), 21.8(CH$_3$CO), 14.10 (CH$_3$), Analysis: C%, 79.96 (Found); 80.40 (Calcd); H%, 9.39 (Found); 9.52 (Calcd).

Synthesis of Scheme 2 Compound 25

The Scheme II compound 24 was dissolved into 2 mL of CH$_2$Cl$_2$ and 0.6 mL of 50% BF$_3$—MeOH was added at about 0° C. to room temperature, while stirred for 4 hr. After concentration, the residue was purified by preparative TLC (petroleum and ether (7+3) as eluting agent) to give 54 mg of product (R$_f$=0.28) (waxy material). NMR: $^1$H, δ(ppm) 5.05 (m, 1H, CH), 3.62–3.16 (m, 4H, OCH$_2$), 2.05 (b, t, 1H, CH$_2$OH), 1.48–1.21 (m, 28H, CH$_2$), 0.86 (t, 3H, $^3$J$_{HH}$=6.9 Hz, CH3),$^{13}$C, δ(ppm) 171.1 (CO), 71.75(CH), 71.3, 68.8, (OCH$_2$), 65.6(CH$_2$OH), 31.9, 29.7, 26.0 22.7(m, CH$_2$), 21.2(CH$_3$CO), 14.2 (CH$_3$).

Scheme 2 Compound 26 and 27

Using the hexadecanyl isopropylidene ether prepared above one conducts the steps shown in Scheme 2 to prepare, in succession, compounds 26 and 27 of Scheme 2. Thus, 50.8 mg (0.15 mM) of scheme 2 compound 25 in 4 ml of THF containing 15 mg of triethylamine and about 1 equivalent of either CIPFA or CLTPFA was stirred at 0° C. for 2 h. After filtration and rotary evaporation of the solvent, the residue, Scheme II compound (7) was purified on silica gel ($CH_2Cl_2:CH_3OH$, 95:5): $^{31}P$ NMR: δ−3.6. Scheme 2 Compound 26 was then hydrolyzed to Scheme 2 Compound 27 by methods known by those skilled in the art. The preparation of methyl chloro(methoxy)thiophosphonoformate (CITPFA) was as follows: Lawesson's reagent (10.7 g, 97%, 0.025 mole) was dissolved in 100 ml of dry toluene at 105° C. followed by 4.0 g (0.02 mole) methyl chloro(methoxy) phosphonoformate (CIPFA) [prepared by the method of Petrov, K. A., Maklyaev, F. L. and Korshunov, M. A. J. Gen. Chem. USSR (Eng. Transl.) 29, 304–308 (1959)]. After 18 hr at reflux, the solvent was removed in vacuum and the residue extracted with hexane. The combined extracts were evaporated leaving the crude product, which was distilled in vacuo to give 0.86 g of a slightly yellow oil, b.p. 40–40.5° C. at 0.075 mm Hg. $^1$H-NMR ($CDCl_3$): δ3.97 (d, $POCH_3$, 3H, $^3J_{PH}$=14), 3.94 (s, $COCH_3$, 3H). $^{13}$C-NMR ($CDCl_3$): δ164.9 (d, CO, $^1J_{PC}$=224), 54.7 (d, $POCH_3$, $^2J_{PC}$=8.5) 54.5 (d, $COCH_3$, $^3J_{PC}$=4.9). $^{31}$P NMR ($CDCl_3$): δ62.4. Calcd for $C_3H_6O_3$ClPS: C, 19.11; H, 3.21; S, 18.80. Found: C, 19.42; H, 3.51; S, 18.80.

Scheme 3 Compound 28 and 29

To a suspension of isopropylidene glycerol (760 mg, 5.214 mmol) and NaH (240 mg, 5.88 mmole) in THF were added tetrabutyl ammonium bromide (168 mg, 0.52 mmol) at room temperature under $N_2$ followed by 4-methoxybenzyl chloride (921 mg, 5.88 mmol). After being refluxed at 65° C. for 14 h, the reaction was quenched with methanol (1 mL) and neutrallized with $NH_4Cl$. The reaction mixture was extracted with ether and the extract was washed with brine, dried over $MgSO_4$, and concentrated in vacuo. The residue was purified with flash chromatography on silica gel with ether and hexane, 1:1. 1.54 g of yellowish oil, with a yield of about 88.6%, was obtained. NMR: $^1$H, δ(ppm) 7.27, 7.25 (dd, 4H, Ph—H), 4.51 (m, 1H, CH), 4.14 (d, 2H, $OCH_2$), 3.96 (m, 4H, $OCH_2$), 3.80 (s, 2H, $PhCH_2$), 1.42 (s, 3H, $CH_3$), 1.36 (s, 3H, $CH_3$), $^{13}$C, □(ppm) 129.3, 130.1, 130.0, 114.1, 113.8 (Ph—C), 109.3 ($C(CH_3)_2$), 74.7 (CH), 73.1, 70.7, 66.9 ($OCH_2$) 55.1($OCH_3$), 26.75, 25.3 ($CH_3$). HRMS: 252.1371(Found); 252.1361 (Calcd); Analysis: C%, 66.85(Found); 66.65(Calcld); H%, 7.58 (Found); 7.99 (Calcld). 3-p-methoxybenzyl-1,2-isopropylidene glyceryl ether, Scheme compound 29 was deprotected in 10 mL 10% acetic acid at 65° C. for 1 hr. The reaction mixture was lyophilized and the residue was purified by flash column chromatography, ethyl acetate as eluting agent. NMR: $^1$H, $^{13}$C consistent with structure.

Scheme 3 Compounds 30, 31 and 32

The R group was hexadecanyl. Scheme 3 compound 29 (1.15 g 4.7 mmol), powdered KOH (1.06 g, 19 mmol), hexadecyl bromide (5.73 g, 20 mmole) and 25 mL toluene were mixed. The reaction mixture was refluxed for 16 hr at room temp. Next, 20 mL of water was added and the oil layer separated. The aqueous layer was washed by toluene and the combined oil phases washed with water brine. After drying over $Na_2SO_4$ and concentrating, 7.1 g of crude product, Scheme 3 Compound 30, was obtained. This was purified by flash chromatography (using hexane and ethyl ether, 9:1). $R_f$=0.44. NMR: $^1$H, $^{13}$C consistent with structure.

To a mixture of Scheme 3 Compound 30 (1.0 g, 1.5 mmol) in $CH_2Cl_2$ (9 mL) and $H_2O$ (0.5 mL) was added DDQ (2,3-dichloro-5,6-dicyanobenzoquinone, 0.36 g, 1.58 mmol). The reaction mixture turned progressively redbrown. After 15 min at room temperature the reaction mixture was filtered, and the filtrate was evaporated in vacuo giving a yellowish solid (0.75 g). This was purified by flash column chromatography (using hexane and ether, 3:1) to give Scheme 3 Compound 31, m.p. 50–51° C. (Y=93.8%) NMR: $^1$H, δ(ppm) 3.68 (m,1H, CH), 3.60–3.39 (m, 8H, $OCH_2$), 2.16–2.13 (dd, 1H, $CH_2OH$), 1.31–1.24 (m, 56H, $CH_2$), 0.86 (t, 6H, $^3J_{HH}$=6.9 Hz); $^{13}$C, δ(ppm), HRMS: 540.5568 (Found); 540.5481 (Calcd); Analysis: C%:, 77.39 (Found); 77.71 (Calcd); H%, 13.23 (Found); 13.42 (Calcd). Scheme 3 Compound 32 (90 mg, 0.28 mM) and 2 ml pyrimidine were dissolved in 1.5 ml chloroform together with 1 equivalent of CIPFA or CLTPFA, which was added at −10° C. The temperature was allowed to rise to r.t., then the reaction mixture was filtered and the filtrate concentrated by rotary evaporation. The residue was purified by column chromatography on silica gel ($CH_2Cl_2:CH_3OH$, 95:5) giving Scheme 3 Compound 32 with $R_f$=0.26. $^{31}$P NMR:

Scheme 3 Compound 27 was demethylated by methods known to those skilled in the arts.

Example 4

Synthesis of Lipophilic Long-chain Coupled PFA and TPFA Trialkyl Esters

Alkyl(O,O-dimethyl)phosphononformate 35

Alkyl chloroformate 34: The triphosgene (1.35 g, 41 mmol) was dissolved in 5 ml of carbon tetrachloride under ice bath, then added into 6 ml of methylene chloride solution containing 9 mmole of dry pyridine and 9 mmole of alcohol 33 by syringe over 30 min at −15° C., after addition removed the cool bath and stirred overnight at r.t. The reaction mixture was filtered and the filtrate was concentrated. The residue was checked by $^1$H-NMR until the identified peak[δ: 4.26 ppm (t)] of product was found replacing the characterized peak [δ: 3.51 (t)] of starting alcohol. The crude product is ready for next reaction without purification.

5.0 mmole of above chloroformate 34 and 12 mL of distilled trimethyl phosphite was heated at 80° C. for 1.5 hr., then stirred at r.t. overnight. The reaction mixture was evaporated in suction. The residue was purified by fresh column chromatography with eluting agent: $CHCl_3$ and $CH_3OH$ (98:2) (monitoring using $I_2$). 1.7–2.7 mmole of pure compound yielded (34–54%).

35a R=$C_7H_{15}$ $^1$H-NMR: δ4.24 (t, 2H), 3.89 (d, 6H, $^3J_{HP}$=10 Hz), 1.31 (m, 2H), 1.26 (bs, 8H), 0.85 (t, 3H); $^{13}$C-NMR: δ167.2 (d, $^1J_{CP}$=155 Hz), 65.3 (d, J=5 Hz), 54.7 (d, J=6 Hz), 14.8 (s); $^{31}$P-NMR: δ−1.67 (m, $^3J_{PH}$=11 Hz).

35b R=$C_8H_{17}$:

$^1$H-NMR: 4.24 (t, 2H), 3.90 (d, $^3J_{HP}$=11 Hz), 1.35 (m, 2H), 1.23 (bs, 10H), 0.85 (t, 3H)

$^{13}$C-NMR: 167.4 (d, $^1J_{CP}$=155 Hz), 67.0 (d, J=5 Hz), 55.0 (d, J=6 Hz), 14.8 (s)

$^{31}$P-NMR: δ−1.68 (m, $^3J_{PH}$=11 Hz)

35c R=$C_{14}H_{29}$:

$^1$H-NMR: δ4.24 (t, 2H), 3.89 (d, 6H, $^3J_{HP}$=10 Hz),1.35 (m, 2H), 1.23 (bs, 22H), 0.85 (t, 3H) $^{13}$C-NMR: δ167.5 (d, 1JCP=156 Hz), 66.4 (d, J=5 Hz), 55.0 (d, J=6 Hz), 14.9 (s).

$^{31}$P-NMR: δ−1.68 (m, $^3J_{PC}$=11 Hz) Microanalysis: for: $C_{17}H_{35}O_5P$, C, 58.27 (Cald); 58.54 (Found); H,10.07(Cald); 10.39 (Found); P, 8.64(Cald); 8.89(Found);

35d R=$C_{16}H_{33}$:

$^1$H-NMR: δ4.24 (t, 2H), 3.90 (d, 6H, $^3J_{HP}$=10 Hz), 1.34 (m, 2H), 1.22 (bs, 26H), 0.84 (t, 3H); $^{13}$C-NMR: δ167.0 (d, $^1J_{CP}$=153 Hz), 66.2 (d, J=Hz); 54.5 (d, J=6 Hz), 14.8 (s);

$^{31}$P-NMR: δ−1.65 (m, $^3J_{PH}$=11 Hz). Microanalysis: for $C_{19}H_{39}O_5P.CHCl_3$, C, 56.00(Cald); 56.16(Found); H, 9.87 (Cald); 9.38(Found); P, 7.22 (Cald); 7.20 (Found);

Alkyl(O,O-dimethyl)thiophosphonoformate 38

9 mmole of Alkyl(O,O-dimethyl)phosphonoformate 35 and 2.0 g (5.0 mmole) of LR were in 25 ml of dry toluene. After the mixture was refluxed for 5 hr under $N_2$. Mixture was concentrated by an evaporator, the yielded residue was extracted with hexane, the extract was dried over $Na_2SO_4$. and concentrated. The residue was purified by fresh column chromatography with hexane and ethyl acetate (6:1) as eluting reagent. Pure thio compounds were obtained with yield (85%).

38a Alkyl=$C_7H_{15}$
$^1$H-NMR: δ4.25 (t, 2H), 3.86 (d, 6H, $^3J_{HP}$=13 Hz), 1.34 (m, 2H), 1.25 (bs, 8H), 0.84 (t, 3H); $^{13}$C-NMR: δ167.2 (d, $^1J_{CP}$=187 Hz), 65.3 (d), 55.5 (d), 14.6 (s);
$^{31}$P-NMR: δ65.34 (m, $^3J_{HP}$=13 Hz); Microanalysis: For $C_{10}H_{21}O_4PS$ $(CH_3COOC_2H_5)_{0.5}$ C, 46.14 (Cald); 46.31 (Found); H, 8.07 (Cald); 8.36 (Found); P, 9.92 (Cald); 10.04 (Found).

38b Alkyl=$C_8H_{17}$:
$^1$H-NMR: δ4.25 (t, 2H), 3.89 (d, 6H, $^3J_{HP}$=13 Hz), 1.34 (m, 2H), 1.26 (bs, 10H), 0.85 (t,3H); $^{13}$C-NMR: δ168.0 (d, $^1J_{CP}$=185 Hz), 65.4 (d, J=5 Hz), 55.7 (d, J=6 Hz), 14.5 (s); $^{31}$P-NMR: δ65.34 (m, JPH=13 Hz).

38c Alkyl=$C_{14}H_{29}$:
$^1$H-NMR: δ4.24 (t, 2H), 3.89 (d, 3JHP=13 Hz), 1.58 (m, 2H), 1.25 (bs, 22H), 0.86(s);
$^{13}$C-NMR: d 168.0 (d, $^1J_{CP}$=185 Hz), 65.4 (d, J=5 Hz), 54.5(d, J=6 Hz); $^{31}$P-NMR: δ65.35 (m, $^3J_{PH}$=13 Hz); Microanalysis: For $C_{17}H_{35}O_4PS$, C, 55.71 (Cald); 55.86 (Found); H, 9.63 (Cald); 10.08 (Found); P, 8.45 (Cald); 8.19 (Found);

38d Alkyl=$C_{16}H_{33}$:
$^1$H-NMR: δ4.24 (t, 2H), 3.87 (d, 6H, $^3J_{HP}$=13 Hz), 1.63 (m, 2H), 1.23 (bs, 26H), 0.86(t, 3H) $^{13}$C-NMR: δ167.4 (d, $^1J_{CP}$=184 Hz), 65.5 (d, J=5 Hz), 54.5 (d, J=6 Hz), 14.4 (s); $^{31}$P-NMR: δ65.4 (m, $^3J_{HP}$=13 Hz) Microanalysis: For $C_{19}H_{39}O_4PS$: C, 57.84 (Cald); 58.11(Found); H, 9.96 (Cald); 10.34 (Found); P, 7.85 (Cald); 7.62 (Found);

O-Alkyl(O,O-dimethyl)phosphonothioformate 42

1, O-methyl chlorothioformate 41d: Oxadecal alcohol 33d (6.0 g, 0.025 mol) and 2.02 mL of pyridine were dissolved in 50 mL of dry diethyl ether in a 250 mL round bottom flask. Thiophosgene (2.875 g, 1.9 mL, 0.025 mol) was added to the mixture above under 0° C. The mixture was stirred for further 30 min. Washed with brine, dried over anhydrous $Na_2SO_4$ and removed of dichloromethane by water aspirator. The residue was distilled to give O-methyl chlorothioformate (5.37 g, yield=48.6%) at 38–41° C./200μ. $^1$H NMR: δ3.76, $^{13}$C NMR: 54.1.

2, O-Methyl(Dimethoxyphosphinyl)thioformate 42d: A solution of O-methyl chlorothioformate 41d (0.55 g, 5 mmol) in dry toluene (8 mL) was added over 10 min to a solution of trimethyl phosphite (0.62 g, 5 mmol) in dry toluene (15 mL) under $N_2$. The mixture was stirred and left for 2 hr at room temperature. The solvent was rotary-evaporated, and the residue was distilled in vacuo, giving a light yellow oil (0.52 g, yield=56.5%) at 80–81° C./100μ. $^1$H-NMR: 64.55 (m, 2H), 3.89 (d, 6H, $^3J_{HP}$=11 Hz), 1.80 (m, 2H), 1.23 (bs, 26H), 0.85(t, 3H) $^{13}$C-NMR: δ212.3 (d, $^3J_{CP}$=223 Hz), 73.1 (d, $^2$J=8 Hz), 54.8 (d, $^3$J=6 Hz), 31.9, 29.7, 29.59, 29.55, 29.5, 29.4, 29.3, 29.1, 27.8, 25.8, 22.7, 14.1; $^{31}$P-NMR: δ-1.28 (m, $^3J_{HP}$=11 Hz).

Methyl(O-alkyl-O-methyl)phosphonoformates 46

Methyl(chloromethoxyphosphinyl)formate 44: To trimethyl phosphonoformate (TMPFA, 16.8 g, 0.1 mol) in dry $CCl_4$ (20 mL) was added at 18° C. finely ground $PCl_5$ (21.9 g, 0.105 mol). After 30 min, the mixture was heated for 1 h at 50° C., then cooled to 18° C. and unreacted $PCl_5$ was decomposed with $SO_2$. After vacuum evaporation, the residue was distilled twice, yielding 12.5 g (72%) product (bp 56–57° C./20 μm Hg). NMR($CDCl_3$): $^1$H δ3.87 (d, $^3J_{PH}$=14 Hz, 3H, $POCH_3$), 3.79 (s, 3H, $COCH_3$); $^{13}$C δ163.6 (d, $^1J_{PC}$=269 Hz, CO), 55.4 (d, $^2J_{PC}$=9 Hz, $CH_3OP$), 53.8 (s, $COOCH_3$); $^{31}$P δ6.80 (s, P=O). Anal. Calcd for $C_3H_6O_4ClP$, C, 20.89; H, 3.51; Cl, 20.55. Found: C, 20.56; H, 3.42; Cl, 20.38.

To a solution of 2.5 mmol of long-chain alcohol in 20 mL of ether was added 2.5 mmol of pyridine, and then added 2.52 mmol of Cl-PFA in 2 mL of ether at 0° C. The reaction mixture was stirred for further 30 min at room temperature. After filtering the precipitation and removing ether, the residue was purified by fresh column chromatography with eluting agent: hexane/ethyl acetate (1/1).

Yield=80–95%.

46a Alkyl=$C_7H_{15}$
$^1$H-NMR: δ4.20 (m, 2H), 3.88 (d, 6H, $^3J_{HP}$=11 Hz), 3.81 (d, 3H, $^3J_{HP}$=1 Hz), 1.65 (m, 2H), 1.23 (bs, 8H), 0.83 (t, 3H); $^{13}$C-NMR: δ166.8 (d, $^1J_{CP}$=270 Hz), 68.5 (d, $^3$J=7 Hz), 54.2 (d, $^2$J=6 Hz), 52.2 (d, $^2$J=6 Hz), 31.5, 30.1, 28.5, 25.1, 22.3, 13.8; $^{31}$P-NMR: δ-2.98 (m, $^3J_{HP}$=7 and 11 Hz); Microanalysis: For $C_{10}H_{21}O_5P(C_6H_{14})_{0.1}$: C, 48.81 (Cald); 48.33 (Found); H, 8.66 (Cald); 8.66 (Found); P, 11.87 (Cald); 11.41 (Found).

46b Alkyl=$C_8H_{17}$:
$^1$H-NMR: δ4.19 (m, 2H), 3.90 (d, 6H, $^3J_{HP}$=11 Hz), 3.84 (s, 3H,), 1.72 (m, 2H), 1.25 (bs, 10H), 0.86 (t, 3H); $^{13}$C-NMR: δ166.8 (d, $^1J_{CP}$=271 Hz), 68.4 (d, $^3$J=7 Hz), 62.6, 54.2 (d, $^2$J=5 Hz), 52.2 (d, $^2$J=6 Hz), 31.5, 30.1, 30.0, 28.9, 28.8, 25.1, 22.4, 13.9; $^{31}$P-NMR: δ-2.97 (m, $^3J_{HP}$=7 and 11 Hz); HRMS: 267.1353 (M+1, Found); 267.1361 (M+1, Calcd). Microanalysis: For $C_{11}H_{23}O_5P(C_6H_{14})_{0.1}$: C, 50.68 (Cald); 50.97 (Found); H, 8.85 (Cald); 9.01 (Found); P, 11.27 (Cald); 11.73 (Found).

46c Alkyl=$C_{14}H_{29}$:
$^1$H-NMR: δ4.18 (m, 2H), 3.85 (d, 6H, $^3J_{HP}$=11 Hz), 3.81 (s, 3H), 1.66 (m, 2H), 1.21 (bs, 22H), 0.83 (t, 3H); $^{13}$C-NMR: δ166.9 (d, $^1J_{CP}$=270 Hz), 68.6 (d, $^3$J=7 Hz), 62.9, 54.5 (d, $^2$J=7 Hz), 52.5 (d, $^2$J=6 Hz), 32.7, 31.9, 30.3, 29.57, 29.55, 29.47, 29.40, 29.28, 28.99, 25.69, 25.22, 22.6, 14.0; $^{31}$P-NMR: δ-2.91 (m, $^3J_{HP}$=7 and 11 Hz); Microanalysis: For $C_{17}H_{35}O_5P(C_6H_{14})_{0.6}$: C, 61.53 (Cald); 61.29 (Found); H, 10.88 (Cald); 11.26 (Found); P, 8.84 (Cald); 9.24 (Found).

46d Alkyl=$C_{16}H_{33}$:
$^1$H-NMR: δ4.19 (m, 2H), 3.89 (d, 6H, $^3J_{HP}$=11 Hz), 3.83 (d, 3H, $^3J_{HP}$=1 Hz), 1.67 (m, 2H), 1.23 (bs, 26H), 0.85 (t, 3H); $^{13}$C-NMR: δ167.0 (d, $^1J_{CP}$=270 Hz), 68.6 (d, $^3$J=7 Hz), 63.1, 54.4 (d, $^2$J=6 Hz), 52.4 (d, $^2$J=5 Hz), 31.9 30.33, 30.28, 29.67, 29.63, 29.61, 29.53, 29.46, 29.34, 29.05, 25.72, 25.28, 22.7, 14.1; $^{31}$P-NMR: δ-2.87 (m, $^3J_{HP}$=7 and 11 Hz); Microanalysis: For $C_{19}H_{39}O_5P(C_6H_{14})_{0.6}$: C, 63.10 (Cald); 63.03 (Found); H, 11.11 (Cald); 10.63 (Found); P, 7.20 (Cald); 6.85 (Found).

46e Alkyl=cis-$C_{16}H_{31}$:
$^1$H-NMR: δ5.28 (m, 2H), 4.15 (m, 2H), 3.86 (d, 6H, $^3J_{HP}$=11 Hz), 3.80 (s, 3H), 1.95 (bs, 4H), 1.65 (m, 2H), 1.24 (bs, 18H), 0.83 (t, 3H); $^{13}$C-NMR: δ166.9 (d, $^1J_{CP}$=270 Hz), 129.7, 68.5 (d, $^3$J=7 Hz), 54.3 (d, $^2$J=6 Hz), 52.3 (d, $^2$J=5 Hz),32.7, 31.8, 30.24, 30.17, 29.63, 29.50, 29.46, 29.42, 27.1, 26.8, 25.7, 25.2, 22.2, 13.9; $^{31}$P-NMR: δ-2.95 (m, $^3J_{HP}$=7 and 11 Hz); HRMS: 377.2449 (M+1, Found); 377.2456 (M+1, Calcd); Microanalysis: For $C_{19}H_{37}O_5P$ $(C_6H_{14})_{0.5}$: C, 62.98 (Cald); 63.17 (Found); H, 10.57 (Cald); 10.40 (Found); P, 7.78 (Cald); 8.15 (Found).

Methyl(O-alkyl-O-methyl)thiophosphonoformate 48

Methyl(chloromethoxythiophosphinyl)formate 45. Lawesson's reagent (10.7 g, 97%, 0.025 mol) in toluene (100 mL) at 105° C. was reacted with DMPFA-Cl (4.0 g, 0.02 mol). When the reaction was complete ($^{31}$P NMR, 18 h), the solvent was evaporated and the residue distilled to yield 0.86 g (21%) pale yellow oil (bp, 40–40.5° C./75 μm Hg). NMR (CDCl$_3$): $^1$H δ3.97 (d, $^3J_{PH}$=14 Hz, 3H, POCH$_3$), 3.94 (s, 3H, COCH$_3$); $^{13}$C δ164.9 (d, $^1J_{PC}$=224 Hz, CO), 54.7 (d, $^2J_{PC}$=9 Hz, CH$_3$OP), 54.5 (d, $^3J_{PC}$=5 Hz, COOCH$_3$); $^{31}$P δ62.40 (s, P=S). Anal. Calcd for C$_3$H$_6$O$_3$ClPS: C, 19.11; H, 3.21; S, 18.80. Found: C, 19.42; H, 3.51; S, 18.80.

To a solution of 2.5 mmol of long-chain alcohol in 20 mL of ether was added 2.5 mmol of pyridine, and then added 2.52 mmol of Cl-TPFA in 2 mL of ether at 0° C. The reaction mixture was stirred for further 30 min at room temperature. After filtering the precipitation and removing ether, the residue was purified by fresh column chromatography with eluting agent: hexane/ethyl acetate (5/1). Yield=85–95%.

48a Alkyl=C$_7$H$_{15}$
$^1$H-NMR: δ4.17 (m, 2H), 3.86 (d, 6H, $^3J_{HP}$=14 Hz), 3.81 (s, 3H), 1.66 (m, 2H), 1.21 (bs, 8H), 0.84 (t, 3H); $^{13}$C-NMR: δ167.8 (d, $^1J_{CP}$=226 Hz), 68.8 (d, $^3J$=7 Hz), 54.4 (d, $^2J$=6 Hz), 52.9 (d, $^2J$=5 Hz), 31.20, 30.1, 28.7, 25.3, 22.5, 14.0; $^{31}$P-NMR: δ63.18 (m, $^3J_{HP}$=10 and 14 Hz); HRMS: 269.0973 (M+1, Found); 269.0976 (M+1, Calcd); Microanalysis: For C$_{10}$H$_{21}$O$_4$PS: C, 46.80 (Cald); 46.75 (Found); H, 8.21 (Cald); 8.41 (Found).

48b Alkyl=C$_8$H$_{17}$:
$^1$H-NMR: δ4.18 (m, 2H), 3.86 (d, 6H, $^3J_{HP}$=14 Hz), 3.83 (s, 3H,), 1.69 (m, 2H), 1.25 (bs, 10H), 0.86 (t, 3H); $^{13}$C-NMR: δ167.8 (d, $^1J_{CP}$=226 Hz), 68.8 (d, $^3J$=7 Hz), 54.3 (d, $^2J$=6 Hz), 52.8 (d, $^2J$=5 Hz), 31.6, 30.2, 30.1, 28.7, 25.6, 25.3, 22.5, 14.0; $^{31}$P-NMR: δ63.20 (m, $^3J_{HP}$=10 and 14 Hz); HRMS: 283.1136 (M+1, Found); 283.1133 (M+1, Calcd); Microanalysis: For C$_{11}$H$_{23}$O$_4$PS: C, 44.77 (Cald); 47.81 (Found); H, 7.89 (Cald); 8.10 (Found).

48c Alkyl=C$_{14}$H$_{29}$:
$^1$H-NMR: δ4.18 (m, 2H), 3.85 (d, 6H, $^3J_{HP}$=14 Hz), 3.82 (s, 3H), 1.67 (m, 2H), 1.22 (bs, 22H), 0.85 (t, 3H); $^{13}$C-NMR: δ167.8 (d, $^1J_{CP}$=226 Hz), 68.7 (d, $^3J$=6 Hz), 54.4 (d, $^2J$=6 Hz), 52.9 (d, $^2J$=5 Hz), 31.9, 30.2, 30.1, 29.63, 29.61, 29.58, 29.51, 29.43, 29.31, 29.05, 25.3, 22.6, 14.1; $^{31}$P-NMR: δ63.18 (m, $^3J_{HP}$=10 and 14 Hz); HRMS: 367.2071 (M+1, Found); 367.2072 (M+1, Calcd).

48d Alkyl=C$_{16}$H$_{33}$:
$^1$H-NMR: δ4.21 (m, 2H), 3.88 (d, 6H, $^3J_{HP}$=13 Hz), 3.83 (d, 3H, $^3J_{HP}$=1 Hz), 1.67 (m, 2H), 1.23 (bs, 26H), 0.85 (t, 3H); $^{13}$C-NMR: δ167.7 (d, $^1J_{CP}$=226 Hz), 68.7 (d, $^3J$=8 Hz), 54.4 (d, $^2J$=6 Hz), 52.9 (d, $^2J$=5 Hz), 31.9, 30.2 30.1, 29.75, 29.68, 29.65, 29.55, 29.47, 29.36, 29.10, 25.4, 22.7, 14.1; $^{31}$P-NMR: δ63.19 (m, $^3J_{HP}$=9 and 13 Hz); HRMS: 395.2384 (M+1, Found); 395.2385 (M+1, Calcd).

48e Alkyl=cis-C$_{16}$H$_{31}$:
$^1$H-NMR: δ5.31 (m, 2H), 4.17 (m, 2H), 3.85 (d, 6H, $^3J_{HP}$=15 Hz), 3.83 (s, 3H), 2.01 (m, 4H), 1.66 (m, 2H), 1.28 (bs, 18H), 0.85 (t, 3H); $^{13}$C-NMR: δ167.7 (d, $^1J_{CP}$=227 Hz), 129.8, 68.7 (d, $^3J$=6 Hz), 54.3 (d, $^2J$=6 Hz), 52.9 (d, $^2J$=4 Hz), 31.9, 30.2, 3.1, 29.73, 29.50, 29.47, 29.44, 29.26, 29.08, 27.2, 26.9, 25.4, 22.3, 14.0; $^{31}$P-NMR: δ63.19 (m, $^3J_{HP}$=10 and 15 Hz); HRMS: 393.2243 (M+1, Found); 393.2228 (M+1, Calcd); Microanalysis: For C$_{19}$H$_{37}$O$_4$PS: C, 58.14 (Cald); 58.33 (Found); H, 9.50 (Cald); 9.69 (Found).

Example 5

Mono-P Ester Monosodium Salts of Lipophilic Long-chain Coupled PFA and TPFA

General Procedure

In a 20 mL flask, 0.5 mmol of the corresponding trialkyl ester was dissolved in 15 mL of dry acetone NaI (75 mg, 0.5 mmol) dissolved in 2 mL acetone was added, and the mixture refluxed for 2 h. It was then cooled, filtered and the precipitate washed with dry acetone until the wash was negative to AgNO$_3$. The final product was dried in a vacuum oven.

Monosodium Salt of Alkyl(O,O-dimthyl)phosphonoformate 36

36a Alkyl=C$_7$H$_{15}$
$^1$H-NMR: δ4.22 (t, 2H), 3.87 (d, 3H, $^3J_{HP}$=12 Hz), 1.35 (m, 2H), 1.23 (b,s, 8H), 0.87 (t, 3H); $^{13}$C-NMR: δ168.5 (d, $^1J_{CP}$=157 Hz), 65.9, 63.4, 14.3; $^{31}$P-NMR: δ–1.90 (q, $^3J_{PH}$=13 Hz);

36b Alkyl=C$_8$H$_{17}$:
$^1$H-NMR: δ, 4.24 (t, 2H), 3.88 (d, 3H, $^3J_{HP}$=13 Hz), 1.36 (m, 2H), 1.24 (b,s,10H), 0.86(t,3H); $^{13}$C-NMR: δ168 (d, $^1J_{CP}$=155 Hz),65.8, 62.7, 14.3; $^{31}$P-NMR: δ–1.89 (q, $^3J_{HP}$=13 Hz);

36c Alkyl=C$_{14}$H$_{Z9}$:
$^1$H-NMR: δ4.23 (t, 2H), 3.90 (d, 3H, $^3J_{HP}$=11 Hz), 1.35 (m, 2H), 1.25 (bs, 22H), 0.86(t, 3H); $^{13}$C-NMR: δ170.0 (d, $^1J_{CP}$=156 Hz), 65.6, 62.9, 14.2; $^{31}$P-NMR: δ, –1.90 (q, $^3J_{PH}$=11 Hz); HRMS: For (M$^-$): 335.1999 (Cald); 335.1987 (Found)

36d Alkyl=C$_{16}$H$_{33}$:
$^1$H-NMR: δ4.25 (t, 2H), 3.91(d, 3H, $^3J_{HP}$=10 Hz), 1.34 (m, 2H), 1.23 (bs, 26H), 0.85 (t, 3H); $^{13}$C-NMR: δ169.0 (d, $^1J_{CP}$=154 Hz), 65.4, 63.4, 14.1; $^{31}$P-NMR: δ–2.82 (q, $^3J_{PH}$=11 Hz); HRMS: For (M$^-$) 363.2300 (Cald); 363.2313 (Found)

Monosodium Salts of Alkyl(O,O-dimethyl) thiophosphonoformates 39

39a Alkyl=C$_7$H$_{15}$
$^1$H-NMR: δ4.12 (t, 2H), 2.21 (t, 3H, $^3J_{HP}$=13 Hz), 1.56 (m, 2H), 1.24 (bs. 8H), 0.85 (t, 3H); $^{13}$C-NMR: δ$^{31}$P-NMR: δ16.44 (q, $^3J_{PH}$=13 Hz);

39b Alkyl=C$_8$H$_{17}$:
$^1$H-NMR: δ4.14 (t, 2H), 2.23 (d, 3H, $^3J_{HP}$=13 Hz), 1.58 (m, 2H), 1.26 (bs, 10H), 0.86 (t, 3H); $^{13}$C-NMR: δ,;$^{31}$P-NMR: δ16.45 (q, $^3J_{PH}$=13 Hz);

39c Alkyl=C$_{14}$H$_{29}$:
$^1$H-NMR: δ4.12 (t, 2H), 2.21 (d, 3H, $^3J_{HP}$=13 Hz), 1.64 (m, 2H), 1.25 (bs, 22H), 0.85 (t, 3H); $^{13}$C-NMR: δ167.4 (d, 175 Hz), 65.4, 22.5, 14.1 (s); $^{31}$P-NMR: δ16.45 (q, $^3J_{PH}$=13 Hz)

39d Alkyl=C$_{16}$H$_{33}$:
$^1$H-NMR: δ4.12 (t, 2H), 2.23 (d, 3H, $^3J_{HP}$=13 Hz), 1.64 (m, 2H), 1.23 (bs, 26H), 0.85 (t, 3H) $^{13}$C-NMR: δ167.0 (d, $^1J_{CP}$=172 Hz), 65.4, 22.6, 14.1(s); $^{31}$P-NMR: δ16.45 (q, $^3J_{PH}$=13 Hz)

Monosodium Salt of Methyl(O-Alkyl-O-methyl) phosphonoformates 47

47a Alkyl=C$_7$H$_{15}$
$^1$H-NMR: δ3.81 (m, 2H), 3.61 (s, 3H,), 1.46 (m, 2H), 1.11 (bs, 8H), 0.69 (t, 3H); $^{13}$C-NMR: δ175.3 (d, $^1J_{CP}$=243 Hz), 68.8 (d, $^3J$=6 Hz), 53.6 (d, $^2J$=4 Hz), 32.7, 31.6, 31.5, 29.7, 26.5, 23.7, 15.1; $^{31}$P-NMR: δ–3.90 (t, $^3J_{HP}$=7); HRMS: 237.0905 (M$^-$, Found); 237.0892 (M$^-$, Calcd).

47b Alkyl=C$_8$H$_{17}$:
$^1$H-NMR: δ3.79 (m, 2H), 3.61 (s, 3H), 1.44 (m, 2H), 1.11 (bs, 10H), 0.69 (t, 3H); $^{13}$C-NMR: δ175.9 (d, $^1J_{CP}$=243 Hz), 69.3 (d, $^3J$=6 Hz), 54.1 (d, $^2J$=4 Hz), 33.4, 32.5, 30.71, 30.62, 27.1, 24.3, 15.7; $^{31}$P-NMR: δ–3.92 (t, $^3J_{HP}$=7); HRMS: 251.1054 (M$^-$, Found); 251.1048 (M$^-$, Calcd).

47c Alkyl=C$_{14}$H$_{29}$:
$^1$H-NMR: δ3.78 (m, 2H), 3.58 (s, 3H), 1.43 (m, 2H), 1.11 (bs, 22H), 0.67 (t, 3H); $^{13}$C-NMR: δ175.3 (d, $^1J_{CP}$=242 Hz), 68.4 (d, $^3J$=7 Hz), 53.2 (d, $^2J$=4 Hz), 33.7, 32.0, 31.58, 31.51, 31.42, 31.18, 31.04, 27.2, 24.3, 15.5; $^{31}$P-NMR: δ−4.70 (t, $^3J_{HP}$=6 Hz); HRMS: 335.1994 (M$^-$, Found); 335.1987 (M$^-$, Calcd).

47d Alkyl=$C_{16}H_{33}$:
$^1$H-NMR: δ3.81 (m, 2H), 3.57 (s, 3H), 1.44 (m, 2H), 1.13 (bs, 26H), 0.71 (t, 3H); $^{13}$C-NMR: δ172.4 (d, $^1J_{CP}$=242 Hz), 65.4, 50.2 (d, $^2J$=5 Hz), 30.9, 29.02, 28.91, 28.87, 28.84, 28.80, 28.75, 28.68, 28.29, 27.86, 24.4, 21.5, 12.6;
$^{31}$P-NMR: δ−4.37 (t, $^3J_{HP}$=7); HRMS: 363.2317 (M$^-$, Found); 363.2300 (M$^-$, Calcd).

47e Alkyl=cis-$C_{16}H_{31}$:
$^1$H-NMR: δ5.15 (m, 2H), 3.76 (m, 2H), 3.58 (s, 3H), 1.95 (bs, 4H), 1.83 (m, 4H), 1.41 (m, 2H), 1.13 (bs, 18H), 0.71 (t, 3H); $^{13}$C-NMR: δ175.2 (d, $^1J_{CP}$=241 Hz), 131.2, 131.1, 68.2 (d, $^3J$=6 Hz), 53.0 (d, $^2J$=5 Hz), 33.4, 31.99, 31.91, 31.78, 31.42, 31.40, 31.34, 31.04, 30.99, 28.8, 28.4, 27.1, 23.8, 15.3;
$^{31}$P-NMR: δ−4.39 (t, $3J_{HP}$=6 Hz); HRMS: 361.2145 (M$^-$, Found); 361.2144 (M$^-$, Calcd).

Ammonium Salt of Methyl(O-alkyl-O-methyl) thiophosphonoformates 49

In a 5 mL flask, methyl(O-Alkyl-O-methyl) thiophosphonoformates (0.05 mmol) was dissolved in t-butyl amine (1.0 mL). The mixture was stirred at room temperature for 4 hr and monitored by $^{31}$P NMR. Extra t-butyl amine was removed in vacuo and further in vacuum oven overnight. Yield=85–95%.

49a Alkyl=$C_7H_{15}$
$^1$H-NMR: δ4.03 (m, 2H), 3.71 (s, 3H), 1.60 (m, 2H), 1.38 (bs, 12H), 1.27 (bs, 8H), 0.85 (t, 3H); $^{13}$C-NMR: δ174.1 (d, $^1J_{CP}$=192 Hz), 68.2 (d, $^3J$=6 Hz), 52.4 (d, $^2J$=5 Hz), 51.7, 31.80, 30.6, 30.5, 29.3, 25.8, 22.6, 14.1; $^{31}$P-NMR: δ47.91 (t, $^3J_{HP}$=9 Hz);

49b Alkyl=$C_8H_{17}$:
$^1$H-NMR: δ4.07 (m, 2H), 3.72 (s, 3H), 1.60 (m, 2H), 1.38 (bs, 12H), 1.27 (bs, 10H), 0.84 (t, 3H); $^{13}$C-NMR: δ173.9 (d, $^1J_{CP}$=192 Hz), 68.2 (d, $^3J$=6 Hz), 52.0, 51.6 31.8, 30.54, 30.49, 29.24, 27.9, 25.7, 22.6, 14.0; $^{31}$P-NMR: δ48.08 (t, $^3J_{HP}$=8 Hz); HRMS: 267.0831 (M$^-$, Found); 267.0820 (M$^-$, Calcd).

49c Alkyl=$C_{14}H_{29}$:
$^1$H-NMR: δ4.05 (m, 2H), 3.72 (s, 3H), 1.60 (m, 2H), 1.41 (bs, 12H), 1.23 (bs, 22H), 0.84 (t, 3H); $^{13}$C-NMR: δ174.0 (d, $^1J_{CP}$=192 Hz), 68.1 (d, $^3J$=6 Hz), 52.4 (d, $^2J$=6 Hz), 31.8, 30.9, 30.6, 29.3, 25.7, 22.6, 15.3, 14.1; $^{31}$P-NMR: δ48.10 (t, $^3J_{HP}$=9 Hz); HRMS: 351.1774 (M$^-$, Found); 351.1759 (M$^-$, Calcd).

49d Alkyl=$C_{16}H_{33}$:
$^1$H-NMR: δ4.06 (m, 2H), 3.73 (s, 3H), 1.63 (m, 2H), 1.44 (bs, 12H), 1.24 (bs, 26H), 0.85 (t, 3H); $^{13}$C-NMR: δ174.0 (d, $^1J_{CP}$=192 Hz), 68.1 (d, $^3J$=6 Hz), 52.3, 31.8, 30.9, 30.6, 30.5, 29.26, 27.91, 25.7, 22.6, 15.3, 14.1; $^{31}$P-NMR: δ48.29 (t, $^3J_{HP}$=9 Hz).

49e Alkyl=cis-$C_{16}H_{31}$:
$^1$H-NMR: δ5.20 (m, 2H), 4.06 (m, 2H), 3.71 (s, 3H), 2.03 (bs, 4H), 1.64 (m, 2H), 1.44 (bs, 12H), 1.23 (bs, 18H), 0.85 (t, 3H); $^{13}$C-NMR: δ174.2 (d, $^1J_{CP}$=192 Hz), 131.2, 68.4 (d, $^3J$=6 Hz), 53.0 (d, $^2J$=5 Hz), 33.4, 31.92, 31.90, 31.73, 31.40, 31.38, 31.34, 31.04, 30.99, 28.75, 28.39, 27.1, 23.8, 15.3; $^{31}$P-NMR: δ48.13 (t, $^3J_{HP}$=8 Hz);

Example 6

Disodium Salts of Long-chain Coupled PFA and TPFA

Disodium Salt of Alkyl Phosphonoformates 37

0.50 mmole of alkyl phosphonoformate and excess BTMS were heated to reflux for 3 hr under $N_2$, then evaporate the excess BTMS. The residue was treated by 1N NaOH until pH=9–10, Lypholized, then recrystallization from methanol or water.

37d Alkyl=$C_{16}H_{33}$:
$^1$H NMR: δ4.14 (t, 2H), 1.36 (m, 2H), 1.23 (bs, 26H), 0.85 (t, 3H); $^{13}$C NMR: δ167.5 (d, $^1J_{CP}$=164 Hz); $^{31}$P NMR: δ−4.99 (s).

Disodium Salt of Alkyl Thiophosphonoformates 40

0.25 mmole of alkyl thiophosphonoformate was dissolved in CHCl$_3$ and CH$_3$OH (1+1), then 0.5 mmole of NaOCH$_3$ Methanol solution was added under $N_2$ at −10° C., stirred for 3 hr, evaporated the solvents and 10 mL of fresh methanol was added then stood at r.t. under $N_2$ until the disodium salt precipitated.

40d Alkyl=$C_{16}H_{33}$:
$^1$H-NMR: δ4.12 (t, 2H), 1.64 (m, 2H), 1.23 (bs, 26H), 0.85 (t, 3H) $^{13}$C-NMR: δ167.0 (d, $^1J_{CP}$=183 Hz), 65.4, 22.6, 14.1(s); $^{31}$P-NMR: δ7.62 (s).

Disodium Salt of Methyl(O-Alkyl-O-methyl) phosphonoformates 50

In a 5 mL flask, methyl(O-Alkyl-O-methyl) phosphonoformates 46 (0.49 mmol) was chilled with ice. 0.2 mL of cold 10 N NaOH was added dropwise. The cloudy mixture was stirred at room temperature for 30 min and monitored by $^{31}$P NMR. Then, 20 mL of methanol was added and white precipitation was immediately formed. The product was filtered and dried in vacuum oven. Yield= 90–95%.

50b Alkyl=$C_8H_{17}$:
$^1$H-NMR: δ3.67 (m, 2H), 1.44 (m, 2H), 1.08 (bs, 10H), 0.67 (t, 3H); $^{13}$C-NMR: δ179.0 (d, $^1J_{CP}$=229 Hz), 66.8 (d, $^3J$=5 Hz),32.3, 31.40, 31.33, 29.66, 29.60, 26.1, 23.2, 14.6; $^{31}$P-NMR: δ−1.95 (t, $^3J_{HP}$=7 Hz);

50c Alkyl=$C_{14}H_{29}$:
$^1$H-NMR: δ3.66 (m, 2H), 1.42 (m, 2H), 1.08 (bs, 22H), 0.67 (t, 3H); $^{13}$C-NMR: δ178.7 (d, $^1J_{CP}$=229 Hz), 66.2 (d, $^3J$=5 Hz),32.2, 31.0, 30.0, 29.65, 29.27, 27.48, 27.15, 25.8, 22.6, 14.1; $^{31}$P-NMR: δ−1.95 (t, $^3J_{HP}$=7 Hz);

50e Alkyl=cis-$C_{16}H_{31}$:
$^1$H-NMR: δ5.28 (m, 2H), 3.67 (m, 2H), 1.86 (m, 4H), 1.43 (m, 2H), 1.10 (bs, 18H), 0.68 (t, 3H); $^{13}$C-NMR: δ178.5 (d, $^1J_{CP}$=229 Hz), 130.55, 130.42, 66.1 (d, $^3J$=5 Hz), 32.2, 31.0, 30.0, 29.64, 29.28, 27.46, 27.13, 25.8, 22.5, 14.1; $^{31}$P-NMR: δ−1.96 (t, $^3J_{HP}$=7 Hz).

Example 7

Biological Methods

Investigation of the anti HHV-8 activity of the pyrophosphate analogues of the present invention was performed in collaboration with Dr. Robert H. Shoemaker of the Developmental Therapeutics Program of the National Cancer Institute.

Assay Set-Up

1. BCBL-1 cells were counted by the trypan blue dye exclusion method, and the cell count/mL was determined. Cells were pelleted by centrifugation and washed once with PBS to minimize the basal level of virus released from untreated cells which spontaneously enter the lytic cycle and release virus.

2. Cells were resuspended in fresh media and adjusted to a cell density of 1×10$^5$ per mL. Cells were then plated in the interior wells of 96-well round-bottom microtiter plates in a volume of 50 μL per well.

3. The phorbol ester TPA was added to appropriate wells in a volume of 50 μL per well to yield a final concentration of 20 ng/mL. Medium was added in place of TPA in three wells to serve as a negative control.

4. Test compounds were diluted in DMSO to a stock concentration which is 400× the desired high concentration. These compounds were further diluted in complete medium in 1.2 mL titertubes to yield a solution which is 2× the desired high concentration. Serial half-log dilutions of this solution were performed in complete medium to yield a total of 6 test concentrations for each test compounds. Compounds dilutions were added to appropriate wells of the microtiter plate in a volume of 100 μL per well. Medium containing no test compound was added to the virus control and cell control wells. In addition, 200 μL medium containing no test compound was added to the exterior wells of the plate.

5. Plates were incubated at 37° C. in a humidified $CO_2$ incubator until day 6 post drug addition.

Determination of Compound Efficacy and Toxicity

1. Plates were removed from the incubator, and the cells were pelleted by centrifugation. Supernatant samples (100 μL) were removed from each well and transferred into 96-well storage plates. The remaining supernatant was carefully removed from each well and discarded. Plates were washed again with PBS to ensure that the amount of test compound remaining in the wells is insignificant. Cell pellets were resuspended in 200 μL of complete medium.

2. XTT stain was prepared, and 50 μL of the stain was added to each well of the plates. Plates were incubated at 37° C. in a humidified $CO_2$ incubator for 4 hours or until sufficient color development has occurred. Plates were read on UVMax microtiter plate reader at a wavelength of 450/650 nm. Toxicity of test compound was determined by comparing the optical density of test wells with that of control wells to give the percent cell control (%CC).

3. Pronase was added to the supernatant samples to a final concentration of 0.75 mg/mL to degrade DNA which has been released by deadcells. Encapsidated DNA from intact virions was not affected by this treatment. Samples were incubated at 37° C. for 30 minutes. Supernatant samples were then treated with 1 Unit of DNase per well and incubated at 37° C. for 60 minutes. DNase was inactivated by heating samples to 95° C. for 15 minutes.

4. PCR reaction mixtures were prepared from reagents provided in the PE Applied Biosystems Taqman PCR Reagent Kit according to manufacturer's directions. Total reaction volumes were 50 μL. Master reaction mix was dispensed into optical PCR tubes in a volume of 47 μL. Samples (3 μL) were added to the reaction mix and mixed thoroughly.

5. Reaction plates were loaded into a PE Applied Biosystems 7700 Sequence Detector, and a run cycle was initiated using the manufacturer's recommended PCR condions. These conditions may be adjusted during development of this assay to optimize virus yield in control wells.

6. A standard curve prepared from known copy numbers of DNA isolated from BCBL-1 cells and amplified was run with each plate in order to quantitate the DNA copy number in each original sample. The efficacy of the compound was determined by comparing DNA copy numbers from test wells with those of control wells to give the percent viral control (%VC).

Initial Screening of Pyrophosphate Analogues

Tables II and III summarize some compounds that exhibited moderate to high levels of antiviral activity after initial screening at a single dose (denoted as HTC (μM) in Table II).

TABLE II

| ID # | General Formula | R | X | HTC (μM) | % VC | % CC | Activity |
|---|---|---|---|---|---|---|---|
| 1 | I | $R_{1,2,3}$ = Na | $X_5$ = S; $X_{1,2,3,4}$ = O | 200 | 5.3 | 84.4 | active |
| 2 | I | $R_{1,2,3}$ = Me | $X_4$ = S; $X_{1,2,3,5}$ = O | 200 | 23.4 | 89.2 | moderate |
| 3 | I | $R_{1,3}$ = Me; $R_2$ = Na | $X_4$ = S; $X_{1,2,3,5}$ = O | 200 | 28.8 | 78.7 | moderate |
| 4 | I | $R_{1,2,3}$ = Me | $X_{4,5}$ = S; $X_{1,2,3}$ = O | 200 | 21.5 | 64.9 | moderate |
| 5 | I | $R_{1,2,3}$ = Me | $X_{3,4}$ = S; $X_{1,2,5}$ = O | 200 | 17.7 | 67.1 | moderate |
| 6 | I | $R_{1,2,3}$ = Na | $X_{1,5}$ = S; $X_{2,3,4}$ = O | 200 | 0.9 | 77.8 | active |
| 7 | I | $R_{1,2,3}$ = Na | $X_{1,4,5}$ = S; $X_{2,3}$ = O | 200 | 7.3 | 76.6 | active |
| — | I | $R_1$ = $CH_2(R_4)CH(R_5)CH_2$; $R_{2,3}$ = Me; $R_{4,5}$ = $C_{15}H_{31}CO$ | $X_{1,2,3,4,5}$ = O | 100 | 3.7 | 61.7 | active |
| 8 | I | $R_1$ = Me; $R_2$ = Na; $R_3$ = $C_{14}H_{29}$ | $X_{1,2,3,4,5}$ = O | 50 | 27.0 | 69.5 | moderate |
| 9 | II | $R_{6,7}$ = Na | $X_6$ = $CH_2$ | 200 | 14.2 | 97.3 | active |
| 10 | II | $R_{6,7}$ = Me | $X_6$ = $NNHX_7$; $X_7$ = 2-Me-4-$NO_2Ph$ | 200 | 2.6 | 53.2 | active |
| 11 | III | $R_8$ = $OR_9$; $R_{9,10}$ = DCHA; $R_{11}$ = H | $X_8$ = Cl; $X_9$ = F | 100 | 19.7 | 65.8 | moderate |
| 12 | IV | $R_{12}$ = DCHA; $R_{13}$ = H | $X_{10}$ = $NNHX_{11}$; $X_{11}$ = 2,4-$(NO_2)_2Ph$ | 200 | 0.3 | 71.6 | active |

TABLE III

| General Formula | R | X | $IC_{50}$ (μm) | $TC_{50}$ (μm) | TI | Activity |
|---|---|---|---|---|---|---|
| I | $R_{1,2}$ = DCHA; $R_2$ = Me | $X_5$ = S; $X_{1,2,3,4}$ = O | >200 | >200 | 4.8 | moderate |

Twelve compounds exhibiting moderate to high antiviral activity in the initial screening were tested again at six different concentrations (as described above) to determine the therapeutic index (TI), wherein TI=$IC_{50}$/$TC_{50}$. Compounds having a TI>10 were considered active, those have a TI>1.5 but <10 were categorized as moderate, and those having a TI<1.5 were considered inactive. The results of one such round of testing is presented below in Table IV:

TABLE IV

| Compound/ID# | IC$_{50}$ ($\mu$M) | TC$_{50}$ ($\mu$M) | TI | Activity |
|---|---|---|---|---|
| Foscarnet | 7.7* | >300 | >38.9 | active |
| 1 | 1.9 | >200 | >105.8 | active |
| 2 | >200 | >200 | NA | inactive |
| 3 | 2.44 | >200 | >82.0 | active |
| 4 | >200 | >200 | NA | inactive |
| 5 | >200 | >200 | NA | inactive |
| 6 | 12.78 | >200 | >15.6 | active |
| 7 | 1.61 | >200 | >124.2 | active |
| 8 | 1.02 | 63.4 | 62.2 | active |
| 9 | 1.75 | >200 | >114.3 | active |
| 10 | 34.45 | >200 | >5.8 | moderate |
| 11 | 87.7 | >200 | >2.3 | moderate |
| 12 | 12.67 | >200 | >15.8 | active |

*average value of six separate tests

These data demonstrate that several of the pyrophosphate analogues tested, e.g., ID#s 1, 3, 7, 8, and 9, were considerably more potent than Foscarnet against HHV-8. The cumulative results of several rounds of antiviral testing are present below in Table V.

TABLE V

| Compound ID# | Test #1 | Test #2 | Test #3 | Test #4 |
|---|---|---|---|---|
| 1 | active | active | active | active |
| 2 | moderate | inactive | inactive | inactive |
| 3 | moderate | inactive | active | inactive |
| 4 | moderate | active | inactive | moderate |
| 5 | moderate | inactive | inactive | moderate |
| 6 | active | moderate | active | active |
| 7 | active | inactive | active | inactive |
| 8 | moderate | moderate | active | active |
| 9 | active | moderate | active | active |
| 10 | active | moderate | moderate | active |
| 11 | moderate | inactive | moderate | moderate |
| 12 | active | moderate | active | moderate |

The following references, discussed above, are all incorporated herein by reference: U.S. Pat. No. 5,183,812 to McKenna; D. W. Hutchinson, et al., "Synthesis and Biochemical Properties of Some Pyrophosphate Analogues", Biosphosphates and Their Analogues-Synthesis, Structure, Metabolism and Activity, K. S. Bruzik and W. J. Stec (Eds.), Elsevier Science Publishers, B. V., 1987, 441–450; Helgstrands, et al., *Science*, 201:819–821 (1978)); J. Levillain, et. al., *J. Am. Chem. Soc.* 115:8444–8446, 1993; L. V. Kovalenko, et al., *Russian J. General Chemistry* 64, Part 1, 1456–1459, 1994); D. W. Grisley, Jr., *J. Org. Chem.* 26, 2544–2546, 1961; U.S. Pat. No. 5,072,032 to C. E. McKenna, et al.; Irwin B. Douglass, *J. Am. Chem. Soc.* 78:6070 (1956); S. Masson et al., *Tetrahedron Lett.* 31 1151 (1990); Ryu, et al, *J. Med. Chem.* 25, 1322–1329 (1982); M. Fuji, et al., *J. Org. Chem.*, 62, 6804 (1997); K. Hostetler, et al., *Antiviral Research*, 31, 59–67 (1996); and Dieter Martin and Wolfgang Mocke, *Chemishe Berichte*, 98 (7), 2059 (1965).

Although the foregoing invention has been described in some detail by way of illustration and example for purposes of clarity and understanding, it will be obvious that various modifications and changes which are within the knowledge of those skilled in the art are considered to fall within the scope of the appended claims. For example, the compounds and compositions of this invention are proposed for use in standard assays for HIV-1 reverse transcriptase. The procedures therefor that can be used, mutatis mutandis, are described in McKenna U.S. Pat. No. 5,072,032, the disclosure of which is incorporated herein by reference. They also are proposed for use in the treatment of other herpes virus infections, in AIDS patients, in medical uses such as chemotherapy, and in agricultural uses such as pesticides.

What is claimed is:

1. A compound having formula I

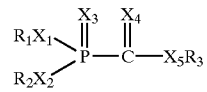

wherein $R_1$ is a cation, $C_1$–$C_{16}$ alkyl or polyalcohol derivative having the general formula $CH_2(R_4)CH(R_5)CH_2$—, wherein $R_4$ and $R_5$ are each independently $C_1$–$C_{16}$ alkoxy or O-acyl $C_1$–$C_{16}$ alkyl; $R_2$ and $R_3$ are each independently cation or $C_1$ to $C_{16}$ alkyl; $X_2$ is oxygen; and $X_1$, $X_3$, $X_4$, and $X_5$ are each independently sulfur or oxygen, provided at least one of (a), (b), (c) or (d) applies:

(a) $R_3$ is $C_7$–$C_{16}$ alkyl; or (b) $X_1$ is sulfur; or (c) $X_3$ and $X_4$ are sulfur; or (d) $R_1$ is $C_7$–$C_{16}$ alkyl and $X_3$ is sulfur.

2. The compound of claim 1, wherein $X_1$, $X_2$, $X_4$, and $X_5$ are oxygen, $X_3$ is sulfur, $R_1$ is $C_7$–$C_{16}$ alkyl and $R_2$ is a cation having the formula $NH_2(CH_3)(t$-$Bu)$.

3. An antivirally active compound or intermediate thereof having formula I

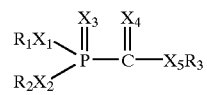

wherein $R_1$ is sodium, dicyclohexylammonium (DCHA), or methyl, $R_2$ is sodium, DCHA, or methyl; $R_3$ is sodium, methyl, or $C_{14}H_{29}$; $X_2$ is oxygen, and $X_1$, $X_3$, $X_4$, and $X_5$ are each independently sulfur or oxygen provided at least one of $X_1$, $X_3$, $X_4$, and $X_5$ is oxygen, and at least one of (a), (b), or (c) applies;

(a) $R_3$ is $C_{14}H_{29}$; or (b) $X_1$ is sulfur; or (c) $X_3$ and $X_4$ are sulfur.

4. The compound of claim 3, wherein $X_1$, $X_2$, $X_3$, $X_4$, and $X_5$ are oxygen, $R_1$ is a polyalcohol derivative having the formula $CH_2(C_{15}H_{31}COO)CH(C_{15}H_{31}COO)CH_2$—; $R_2$ is sodium, and $R_3$ is methyl.

5. The compound of claim 3, wherein $X_1$, $X_2$, $X_3$, $X_4$, and $X_5$ are oxygen, $R_1$ is methyl, $R_2$ is sodium, and R3 is $C_{14}H_{29}$.

6. A phosphonoformic acid derivative, selected from the group consisting of:

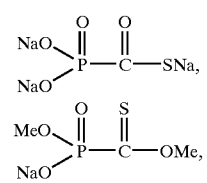

-continued
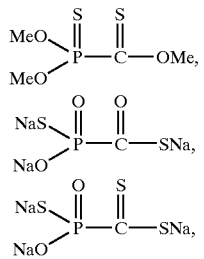
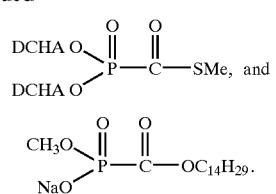
* * * * *